US012502534B2

(12) United States Patent
Finkelstein et al.

(10) Patent No.: US 12,502,534 B2
(45) Date of Patent: Dec. 23, 2025

(54) SYSTEMS AND METHODS TO PROMOTE TISSUE HEALTH VIA ELECTRICAL STIMULATION

(71) Applicant: NEURO20 TECHNOLOGIES CORP., Oldsmar, FL (US)

(72) Inventors: Michael Howard Finkelstein, Tampa, FL (US); Dennis Michael Schmitt, Tampa, FL (US); Jana Schmitt, Tampa, FL (US)

(73) Assignee: Neuro20 Technologies Corp., Oldsmar, FL (US)

( * ) Notice: Subject to any disclaimer, the term of this patent is extended or adjusted under 35 U.S.C. 154(b) by 0 days.

(21) Appl. No.: 18/665,231

(22) Filed: May 15, 2024

(65) Prior Publication Data

US 2024/0299741 A1 Sep. 12, 2024

Related U.S. Application Data

(63) Continuation of application No. PCT/US2022/049678, filed on Nov. 11, 2022.

(Continued)

(51) Int. Cl.
*A61N 1/36* (2006.01)
*A47G 9/00* (2006.01)

(Continued)

(52) U.S. Cl.
CPC ........... *A61N 1/328* (2013.01); *A47G 9/0238* (2013.01); *A61N 1/0452* (2013.01);

(Continued)

(58) Field of Classification Search
CPC .... A61N 1/328; A61N 1/0452; A61N 1/0484; A61N 1/36031; A61N 1/36034; A47G 9/0238; A47G 9/007
See application file for complete search history.

(56) References Cited

U.S. PATENT DOCUMENTS 3,576,458 A * 4/1971 Smith, Jr. ................ H01T 2/02 218/147
4,657,023 A * 4/1987 Kuhn .................... A61B 5/257 607/152

(Continued)

FOREIGN PATENT DOCUMENTS

KR 2008 0045923 A 5/2008

OTHER PUBLICATIONS

PCT International Search Report and Written Opinion, regarding International Application No. PCT/US2022/049678, mailed Feb. 16, 2023, 16 pages.

(Continued)

*Primary Examiner* — David Hamaoui
*Assistant Examiner* — Rumaisa Rashid Baig
(74) *Attorney, Agent, or Firm* — Knobbe, Martens, Olson & Bear LLP

(57) ABSTRACT

Electrical stimulation systems and methods for preventing and treating pressure ulcers is provided. The system includes a washable sheet with one or more conductive signal pathways and integral or removable electrodes and a connectable controller that cooperates with the sheet and electrodes to provide periodic electrical stimulation to a patient's skin. Various sensors may provide feedback and optional closed-loop control. The electrical stimulation patterns may help maintain tissue health, prevent development or worsening of pressure ulcers, or manage pain.

12 Claims, 25 Drawing Sheets

Related U.S. Application Data

(60) Provisional application No. 63/264,082, filed on Nov. 15, 2021.

(51) Int. Cl.
*A47G 9/02* (2006.01)
*A61N 1/04* (2006.01)
*A61N 1/32* (2006.01)

(52) U.S. Cl.
CPC ....... *A61N 1/0484* (2013.01); *A61N 1/36031* (2017.08); *A61N 1/36034* (2017.08); *A47G 9/007* (2013.01)

(56) References Cited

U.S. PATENT DOCUMENTS 4,679,563 A * 7/1987 Wada .................... A61B 5/259 600/397
5,318,514 A * 6/1994 Hofmann ............... A61N 1/327 604/20
5,336,255 A * 8/1994 Kanare ................ A61N 1/0456 607/152
5,429,240 A * 7/1995 Biebel .................. B65D 43/162 220/255
5,465,440 A * 11/1995 Heptner ............... A47G 9/0246 5/497
5,683,387 A * 11/1997 Garito .................. A61B 17/322 606/41
5,899,922 A * 5/1999 Loos ....................... A61N 1/40 607/2
6,065,154 A * 5/2000 Hulings ................. A61N 1/321 600/389
6,445,955 B1 * 9/2002 Michelson ........... A61N 1/0456 607/46
7,660,636 B2 2/2010 Castel et al.
7,949,403 B2 5/2011 Palermo et al.
8,660,651 B2 2/2014 Castel et al.
8,738,142 B2 5/2014 Palermo et al.
9,390,630 B2 7/2016 Daniels
9,802,039 B2 10/2017 Palermo et al.
10,022,184 B2 * 7/2018 Doll ....................... A61B 18/16
10,143,397 B2 12/2018 Altshuler et al.
10,437,335 B2 10/2019 Daniels
10,698,492 B2 6/2020 Daniels
10,820,718 B1 * 11/2020 Hall ..................... A47C 31/105
11,033,206 B2 6/2021 Roh
11,229,787 B2 1/2022 Daniels et al.
11,844,450 B1 * 12/2023 Peter .................... A47G 9/0238
2002/0047564 A1 * 4/2002 Ham ...................... G02B 26/02 315/169.3
2003/0194832 A1 * 10/2003 Lopata ............... H01R 13/6625 257/E23.079
2006/0009048 A1 * 1/2006 Hsieh ..................... H05K 1/147 439/65
2006/0173523 A1 * 8/2006 Rainey ................. A61N 1/0468 607/152
2008/0215128 A1 * 9/2008 Rainey ................. A61N 1/0452 602/53
2009/0082831 A1 * 3/2009 Paul ................... A61N 1/36031 607/59
2009/0216182 A1 * 8/2009 Lauchard ............. H03K 17/955 604/65
2010/0156811 A1 * 6/2010 Long ..................... G06F 3/0446 345/173
2011/0077728 A1 * 3/2011 Li ........................ A61N 1/0484 607/152
2011/0282164 A1 * 11/2011 Yang .................... B60N 2/0027 702/41
2012/0016440 A1 1/2012 Muccio
2012/0029591 A1 * 2/2012 Simon ...................... A61N 1/40 607/42
2012/0038375 A1 * 2/2012 Kristiansen ............ G01N 27/02 324/694
2012/0144551 A1 6/2012 Guldalian
2012/0158074 A1 * 6/2012 Hall ....................... A61B 5/318 607/5
2012/0183942 A1 * 7/2012 Pastrick ................. G09B 23/28 434/265
2012/0283794 A1 * 11/2012 Kaib .................... A61N 1/3904 607/5
2012/0286703 A1 * 11/2012 Touchi ................... H05H 13/02 315/503
2013/0157511 A1 * 6/2013 Burkiett ................. H01R 11/12 439/625
2014/0073895 A1 * 3/2014 Freeman ................ A61B 5/291 600/382
2014/0083434 A1 * 3/2014 Groteke ............... A61N 1/0456 128/845
2014/0343392 A1 * 11/2014 Yang .................... A61B 5/7221 600/393
2014/0350882 A1 * 11/2014 Everett ................... G01L 25/00 702/98
2015/0012079 A1 * 1/2015 Goroszeniuk ........ A61N 1/0484 607/148
2015/0057734 A1 * 2/2015 Mushahwar .......... A61F 13/069 607/149
2015/0202429 A1 7/2015 Fritzsche
2015/0335876 A1 * 11/2015 Jeffery ................. A61N 1/0492 607/139
2016/0135741 A1 * 5/2016 Chetham .............. A61B 5/0537 600/391
2017/0056644 A1 * 3/2017 Chahine ............. A61N 1/36014
2017/0303849 A1 10/2017 De Sapio
2017/0347923 A1 12/2017 Roh
2017/0356815 A1 * 12/2017 Madden ............... A61B 5/0205
2017/0358235 A1 12/2017 Daniels
2018/0001086 A1 1/2018 Bartholomew
2018/0021184 A1 * 1/2018 Monson ............... H01Q 9/0457 340/573.5
2018/0036531 A1 2/2018 Schwarz
2018/0143686 A1 * 5/2018 An .......................... G06F 3/017
2018/0318583 A1 * 11/2018 Mcbride ................ A61B 5/112
2019/0001135 A1 1/2019 Yoo
2019/0083784 A1 3/2019 Raghunathan
2019/0209831 A1 * 7/2019 Dernebo .............. A61N 1/0484
2019/0282822 A1 * 9/2019 Freeman .............. A61N 1/3987
2019/0298987 A1 * 10/2019 Freeman .................. A61N 1/08
2020/0178887 A1 * 6/2020 Correa Ramírez .. A61B 5/4809
2020/0188653 A1 * 6/2020 Dernebo .............. A61N 1/0476
2020/0197688 A1 * 6/2020 Dernebo ............ A61N 1/36003
2020/0237031 A1 7/2020 Daniels et al.
2020/0353239 A1 11/2020 Daniels et al.
2020/0383836 A1 * 12/2020 Hansson ............. A61F 13/0226
2020/0393905 A1 12/2020 Daniels
2021/0145686 A1 * 5/2021 Oh ....................... A61N 1/0408
2021/0178158 A1 * 6/2021 Siff .................... A61N 1/36021
2021/0244941 A1 8/2021 Daniels et al.
2021/0353181 A1 11/2021 Roh
2021/0393558 A1 * 12/2021 Weihs ....................... A61F 5/32
2022/0288382 A1 9/2022 Daniels
2023/0143788 A1 * 5/2023 Liu ................... G02F 1/134309 349/139
2024/0165400 A1 5/2024 Tellenbach et al.

OTHER PUBLICATIONS

International Search Report and Written Opinion for PCT/US2021/051149 dated Mar. 18, 2022.
Extended European Search Report, regarding EP Patent Application No. 22893657.1, dated Apr. 15, 2025, 8 pages.

* cited by examiner

SYSTEMS AND METHODS TO PROMOTE TISSUE HEALTH VIA ELECTRICAL STIMULATION

INCORPORATION BY REFERENCE TO ANY PRIORITY APPLICATIONS

This application is a continuation of International PCT Application No. PCT/US2022/049678 filed Nov. 11, 2022, which claims priority to U.S. Provisional Application No. 63/264,082 filed Nov. 15, 2021, the entire content of each of which is hereby incorporated by reference herein. This application is related to WIPO Publ. No. WO 2022/061250 published on Mar. 24, 2022, the entire content of which is hereby incorporated by reference herein.

FIELD

Electrical muscle stimulation (EMS) uses electrical impulses to elicit muscle contraction via electrodes applied to the skin over target musculature. EMS is a tool useful for, among other things, maintaining tissue health, pressure ulcer prevention, pain management, and testing and evaluation of the neuromuscular system.

BACKGROUND

A pressure ulcer (also known as “bed sore,” “pressure sore,” or “decubitus ulcer”) is a tissue abnormality or lesion resulting from pressure imposed upon soft tissue underlying skin, fat, fascia, muscle, bone, or any combination thereof. Following prolonged periods of loading in compression, tension and/or shear, the soft tissue positioned between a bony prominence (e.g. the ischial tuberosities, trochanter, shoulder blades, sacrum) and an external surface (e.g. bed, wheelchair) begins to deform and break down. The sustained deformation of tissue and the occlusion of capillaries and ischemic reduction of blood flow to the loaded tissue region leads to a reduction of oxygen, nutrients, and removal of metabolic waste products, resulting in soft tissue breakdown. While the majority of pressure ulcers are located on the torso bony prominences, other locations such as the wrist, ankle malleolus, clavicles, ears, and nose can also be affected by pressure ulcers, particularly from medical devices attached to these locations (e.g., masks that include elastic and straps that apply pressure to ears and noses).

Pressure ulcers are typically associated with individuals having compromised mobility or lack of sensation, such as the infirm, elderly and people suffering from stroke, spinal cord injury, bone and joint disease, vascular pathologies, tumors, and diabetes. People in intensive care units, hospital wards, or undergoing long surgical procedures are also at risk of developing pressure ulcers. Some medical devices on the skin can also apply sufficient sustained force to cause a pressure ulcer. For example, a patient lying on a return electrode pad for an extended surgery is at risk of developing a pressure ulcer. Similarly, a brace, splint, cast, collar, or strap can apply pressure to the body and cause a pressure ulcer.

Pressure ulcers affect patients’ quality of life, having detrimental psychological effects and increases in morbidity rates. Approximately 2.5 million people per year develop pressure ulcers, including 7-8% of all patients with paraplegia and 144,000 patients per year in nursing home facilities. They result in 60,000 deaths annually. According to the Agency for Healthcare Research and Quality (AHRQ), pressure ulcers create annual US healthcare costs of $9.1-11 billion, including $20,900-151,700 per ulcer to hospitals and $43,100 per ulcer to Medicare. An average 300-bed acute facility with a 2.4% incidence rate spends $14 million per year on pressure ulcer prevention and treatment. The Centers for Medicare & Medicaid Services (CMS) spends $22 billion a year on pressure ulcers as a secondary diagnosis.

Currently available products focus on prevention and early detection, typically by assessing and reducing the likelihood of developing pressure ulcers implementing early prevention measures. Passive preventative techniques include establishing a healthy skin microclimate and using materials to reduce pressure, friction, and shear, such as foam surfaces. Active prevention seeks to periodically reallocate pressure to other tissue. Some active prevention systems seek to cause user movement by triggering an alarm, activating a reminder, or causing discomfort in the patient. Automatic movement systems include fluid (e.g. liquid or air) movement in a mattress or other surface to redistribute body weight and reduce pressure spots. Electrical stimulation or electrical muscle stimulation (EMS) can also be provided, typically with labor intensive handheld devices requiring provider time and expertise, as well as having costly replacement parts.

SUMMARY

Embodiments disclosed herein advantageously provide medical providers the ability to prevent the onset of, or treat existing, various medical conditions, including pressure ulcers. Embodiments disclosed herein include a stimulation sheet configured to be fitted on a hospital patient bed. The stimulation sheet includes multiple electrode pads positioned at strategic locations corresponding to likely locations of certain regions of a patient’s body. The stimulation sheet may include pre-arranged and fixed electrode locations (with different stimulation sheets being made available for different types of patients based on height, weight, or other patient characteristics). In some implementations, the electrode pads may be re-configured and repositioned at different locations. For example, the electrode pads may comprise removable and attachable electrodes or electrode pads.

The stimulation sheet may include a connection interface or connection port configured to operatively couple to a control box or controller unit configured to control electrical stimulation (e.g., initiate and disable stimulation and control stimulation parameters such as amplitude, frequency, intensity, duration, pulse width, etc.). The control box or controller unit may be positioned within a pouch or pocket on a side of the stimulation sheet and the connection interface or port may be located within the pouch. The control box or controller unit may be electrically coupled to the electrodes or electrode pads via cabling (e.g., wires), threading, conductive ink, or other electrical conduits sewn or placed on or within the sheet. The communication conduits extend from the connector interface or port to the various electrodes. The communication conduits may also be machine washable.

In some embodiments, a machine washable bed sheet is described that includes embedded or external machine-washable electrodes or electrode pads shaped, sized and positioned to deliver electrical stimulation specifically to body regions likely to be in contact with the areas of the electrodes or electrode pads. The machine-washable electrodes may be sewn into the bed sheet. Because the bed sheet, including the electrodes, are machine-washable, the bed sheet can be reused for multiple patients (e.g., is not disposable after a single use), thereby reducing supply costs.

In accordance with several embodiments, the electrodes are integrated with the bed sheet and are not separate electrical stimulation devices.

Prevention of onset of pressure ulcers may be the most efficient health outcome and financial cost option. The systems, devices and methods described herein are advantageously designed to give medical providers an effective, low cost, simple to operate system, with protocols that increase the cost efficiency of the entire treatment dosage and greatly reduce financial liabilities for the provider. The electrical stimulation system (e.g., stimulation sheet and controller unit) promotes circulation by contracting the essential tissue surrounding the areas of high pressure that tend to cause pressure ulcers to develop.

As another example, a machine-washable sheet, such as a fitted bed sheet, has embedded or externally attached electrode pads to stimulate tissue surrounding areas of potential pressure ulcer development. The electrode pads can absorb moisture (e.g., sweat) to create an anti-wicking microclimate to further inhibit formation of pressure ulcers. A stimulation control box provides electrical stimulation signals to the electrodes over a signal pathway. The control box can be detachably connected, and can advantageously be moved from one stimulation sheet to another stimulation sheet. In other words, the control box is not limited to use with a single stimulation sheet but can be used interchangeably with multiple different stimulation sheets. Electrode pads or ports may also be removable and attachable to change positioning on the sheet or to move between sheets.

The electrical stimulation system described herein changes and simplifies current pressure ulcer prevention systems by using EMS to redistribute pressure, rather than manual techniques that require costly clinician time and equipment. This lowers variable costs and liabilities while increasing hospitals' operating earnings.

In some aspects, the techniques described herein relate to an apparatus including: a washable non-conductive sheet; one or more washable and conductive electrodes carried by the sheet; a controller configured to provide stimulation signals to the one or more electrodes; and a signal pathway connecting the one or more electrodes to the controller. In some aspects, the one or more electrodes include a plurality of conductive electrodes spaced across the sheet.

In some aspects, the techniques described herein relate to an apparatus, wherein the sheet is sized for a bed, and the plurality of electrodes include a first electrode shaped, sized and positioned to correspond to locations of a left and right scapula, a second electrode shaped, sized and positioned to correspond to locations of a sacrum and left and right trochanters, and third electrode shaped, sized and positioned to correspond to locations of a left and right ischial tuberosity. In some aspects, the one or more electrodes are removably connected to the signal pathway with an electrode connector. In some aspects, the one or more electrodes are configured to absorb moisture. In some aspects, the one or more electrodes include an anti-microbial agent. In some aspects, the anti-microbial agent is silver.

In some aspects, the techniques described herein relate to an apparatus, wherein the signal pathway is selected from the group consisting of: conductive wire, conductive thread, conductive ink, and combinations thereof. In some aspects, the controller is removably connected to the signal pathway with a connector port. In some aspects, the connector port includes a magnetic connection. In some aspects, the connector port includes an outer circuit for connecting to the controller, an inner circuit connected to the signal pathway, and flexible wires connecting the outer circuit to the inner circuit. In some aspects, the outer circuit is an outer PCB and the inner circuit is an inner PCB. In some aspects, the connector port includes a pocket for the controller. In some aspects, the signal pathway of the apparatus includes a first connector port on a first side of the sheet and a second connector port on a second side of the sheet; and the controller is removably connectable to both the first connector port and second connector port.

In some aspects, the techniques described herein relate to an apparatus including: a washable non-conductive sheet; a conductive electrode carried by the sheet; a controller configured to provide stimulation signals to the electrode; a signal pathway connecting the electrode to the controller; and a sensor connected to the controller.

In some aspects, the sensor is selected from the group consisting of a temperature sensor, a pressure sensor, a wetness sensor, and a pH sensor. In some aspects, the sensor is carried by the sheet and connected to the controller via the signal pathway. In some aspects, the sensor is an impedance sensor. In some aspects, the controller is further configured to determine contact, pressure, or tissue wetness from the impedance sensor.

In some aspects, the techniques described herein relate to an apparatus including: a washable non-conductive sheet; one or more conductive electrodes carried by the sheet; a controller configured to provide stimulation signals to the electrode; and a conductive signal pathway carried by the sheet that connects the electrode to the controller. In some aspects, the stimulation signals have a constant current, a frequency of 1-120 Hz, a pulse width of 75-400 microseconds, and a voltage of 7-80 volts.

In some aspects, the techniques described herein relate to a method of reducing a likelihood of pressure ulcer formation, including providing an apparatus including: a washable non-conductive sheet; one or more washable and conductive electrodes carried by the sheet; a controller configured to provide stimulation signals to the one or more electrodes; and a signal pathway connecting the one or more electrodes to the controller, positioning a patient and the sheet such that the electrode is near an area of skin; and with the controller and electrode, applying electrical stimulation to the area of skin.

In some aspects, the electrical stimulation activates muscles and increases blood flow and tissue oxygenation to the area of skin and underlying tissues. In some aspects, the area of skin has a high applied pressure that contributes to formation of a pressure ulcer.

Additional features and advantages will be set forth in the detailed description that follows, and in part will be readily apparent to those skilled in the art from that description or recognized by practicing the apparatus and methods as described herein, including the detailed description that follows, the claims, and the appended drawings.

It is to be understood that both the foregoing general description and the following detailed description are merely exemplary, and are intended to provide an overview or framework for understanding the nature and character of the apparatus and methods as they are claimed. The drawings illustrate various embodiments and together with the description serve to explain the principles and operation.

DETAILED DESCRIPTION

Figure 1:
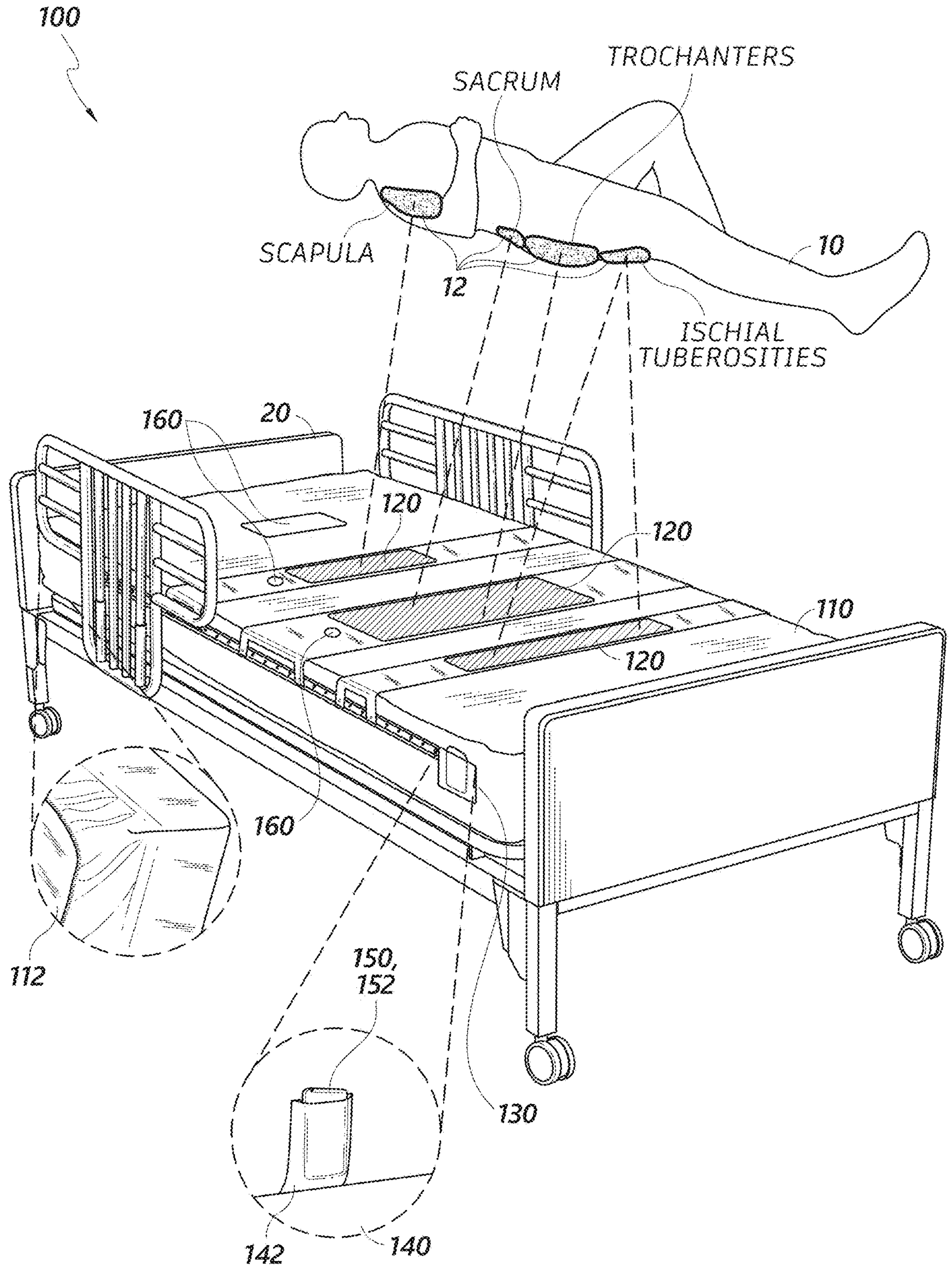
FIG. 1 illustrates an implementation of a stimulation system for incorporation with a patient bed.

As illustrated in FIG. 1, the electrical stimulation system 100 includes a machine-washable sheet 110, such as a fitted bed sheet, with embedded or attached electrode pads 120 to stimulate tissue surrounding target stimulation areas (e.g., areas of potential pressure ulcer development 12). The machine-washable sheet 110 may include fitted elastic corner pockets 112. The electrode pads 120 can absorb moisture (e.g., sweat) to create an anti-wicking microclimate to further inhibit formation of pressure ulcers. The electrical stimulation system 100 also includes a stimulation controller 150, typically in a control box 152, at controller connection site 140 provides electrical stimulation signals to the electrodes 120 over a signal pathway 130. In use, sheet 110 fits over a surface, for example a mattress 20 of a patient bed. The electrode pads 120 are located beneath expected pressure areas 12 on a patient 10 when the patient 10 is lying on top of the sheet 110. Stimulation from the stimulation controller 150 at controller connection site 140 is delivered via signal pathway 130 to the electrode pads 120 to improve blood flow at potential high-risk pressure areas 12 of the patient 10. Optional sensors 160 can collect patient data to monitor progress and/or adjust the provided stimulation signals.

The design and features of the system 100 can be made with variations, such as being separable. In particular, the electrodes 120, sensors 160, and stimulation controller 150 can be removable and attachable with an attachment mechanism. The attachment mechanisms can include pockets or pouches, magnets, hook and loop, adhesive, buttons, snaps, clips, mating pads, and other suitable connectors. This feature allows each component to be disconnected for replacement, disposal, cleaning, and/or optimization. The connection point between an electrode 120 and the sheet 110, the electrode 120 and the signal pathway 130, the stimulation controller 150 and the sheet 110, and the stimulation controller 150 and the electrodes 120 via signal pathway 130 can be independently adapted to connect and interact with any electrode or electrical stimulation device. In some implementations, the stimulation controller 150 is housed within control box 152. The control box 152 can be detachably connected to the signal pathway 130 and/or the sheet 110 at a controller connection site 140, and can be moved from one signal pathway 130 to another signal pathway 130 on the same sheet 110 or a different sheet 110. Electrode pads 120 or ports may also be removable and attachable to change positioning of an electrode 120 on the sheet 110 or to move between sheets 110.

In some implementations, the system 100 has one sheet 110, one electrode 120, one signal pathway 130, and one stimulation controller 150. In some implementations, the system 100 has one sheet 110, three electrodes 120, one signal pathway 130, and one stimulation controller 150. In some implementations, the system 100 has one sheet 110, three electrodes 120, one sensor 160, two signal pathways 130, and one stimulation controller 150. In some implementations, the system has one sheet 110, five electrodes 120, two sensors 160, two signal pathways 130, and one stimulation controller 150. In some implementations, the system has two sheets 110, forty-eight electrodes 120, forty-eight sensors 160, four signal pathways 130, and two stimulation controllers 150. In some implementations, the system 100 includes two sheets 110, five electrodes 120, two sensors 160, four signal pathways 130, and one stimulation controller 150. The modular system 100 can be easily adjusted to meet the needs of a particular use case application so that any number of electrodes and/or sensors can be used. The sensors 160 may be optional in various implementations.

Sheet

In implementations, the sheet 110 is a moisture wicking, shear and friction reducing, washable textile that appropriately positions the electrodes 120 in contact with pressure areas 12 of the patient 10 when the patient 10 is on the sheet 110. In some implementations, the sheet 110 also carries the signal pathway 130, controller connection area 140, stimulation controller 150, and optional sensors 160. These elements are located in or on the sheet 110 in relevant locations, as discussed in further detail below.

As discussed above, pressure ulcers tend to develop as patients sit or recline. Therefore, the sheet 110 is generally sized and shaped to cover seating and/or reclining surfaces 20 (e.g., chairs, beds, exam tables, exercise mats), or portions of seating and/or reclining surfaces that tend to apply pressure to the patient (e.g., the back, sacrum, heel). The sheet 110 can take the form of a fitted sheet, flat sheet, pillowcase, mattress pad, mattress cover, seat cover, seat cushion, cushion cover, exercise mat, and the like. The sheet 110 can be sized to fit the covered surface 20 (e.g., as a standard or oversize fitted hospital bedsheet or wheelchair seat cushion cover), or sized to fit the target anatomy 12 of the patient 10 (e.g., as a mat approximately the size of an adult from knees to shoulders). In some implementations, the sheet 110 is sized to fit around, on, or under another medical device on the skin. For example, the sheet 110 may be a small sheet for holding one electrode 120 against the skin under a splint.

In some implementations, the sheet is a large cover for a large surface 20, such as a bed, sofa, chair, recliner, exam table, surgical table, floor exercise mat, or other seating/reclining surface, having dimensions of 245 cm by 122 cm (96" by 48") or larger. In some implementations, the sheet 110 is a fitted hospital bedsheet with dimensions of approximately 91.5 cm by 223.5 cm (36" by 88"). In some implementations, the sheet 110 is a fitted sheet (FIG. 1, for example), mattress cover, mattress pad, or mattress top for a hospital or residential bed with dimensions of 99 cm by 193 cm (39" by 76" or twin), 99 cm by 203 cm (39" by 80" or twin xl), 137 cm by 193 cm (54" by 76" or double), 152.5 cm by 203 cm (60" by 80" or queen), 185.5 cm by 203 cm (73" by 80" or king), 185.5 cm by 216 cm (73" by 85" or California king), or other standard dimensions. In some implementations, the sheet 110 is a fitted sheet, mattress cover, mattress pad, or mattress top for a neonatal, pediatric, bariatric, or other specialty bed 20. All fitted bedsheets can be made for thin or deep mattresses, having corner pockets, such as corner pocket 112, and sides for a mattress thickness of approximately 5 cm to 46 cm (2" to 18").

In some implementations, the sheet 110 is a pillowcase or pillow with dimensions of approximately 51 cm by 76 cm (20" by 30" or standard) or 51 cm by 91.5 cm (20" by 36" or king), while smaller (e.g., neck or back pillow) and larger (e.g., body pillow) sizes are also contemplated. In some implementations, the sheet 110 is a seat cover, seat cushion, or cushion cover sized to the seating surface 20. Such sheets 110 have dimensions of approximately 30.5 cm by 30.5 cm (12" by 12") up to 91.5 cm by 91.5 cm (36" by 36"), including typical wheelchair seat sizes of 46 cm by 56 cm (18" by 22") and 40.5 cm by 46 cm (16" by 18"). Some implementations are sized to correspond to the target anatomy 12, having dimensions of 5 cm by 5 cm (2" by 2") for small areas such as the heel or elbow, up to approximately 61 cm by 122 cm (24" by 48") for the torso and upper legs of an adult. In some implementations, the sheet 110 has dimensions corresponding to a medical device, such as 8 cm by 13 cm (3" by 5") for use with a brace or splint, 5 cm by 46 cm (2" by 18") for use with a safety belt or strap (e.g., on a table or wheelchair), and 2.5 cm by 25.5 cm (1" by 10") for use with oxygen lines over the cars.

Although these dimensions refer generally to typical adult patients, the sheet 110 is scalable down to shorter and/or smaller individuals such as infants, children, adolescents, teens, and other short stature, as well as scalable up to taller and/or larger individuals such as those with hypertrophy, tumors, obesity, or other conditions. Similarly, the system 100 can use multiple cooperating sheets 110 tightly sized to particular anatomical areas 12, or a single large sheet 110 with multiple electrode regions 120 corresponding to the target anatomy 12. In implementations of the sheet 110 that cover another device or article surface 20 (e.g., splints, mattresses, tables, etc.), the sheet 110 can optionally include elastic bands, straps, ties, or other fasteners to help secure the sheet 110 to the article surface 20. For example, elastic band 216 secures sheet 200 to a surface 20 such as a table, bed, or mattress.

Figure 2A:
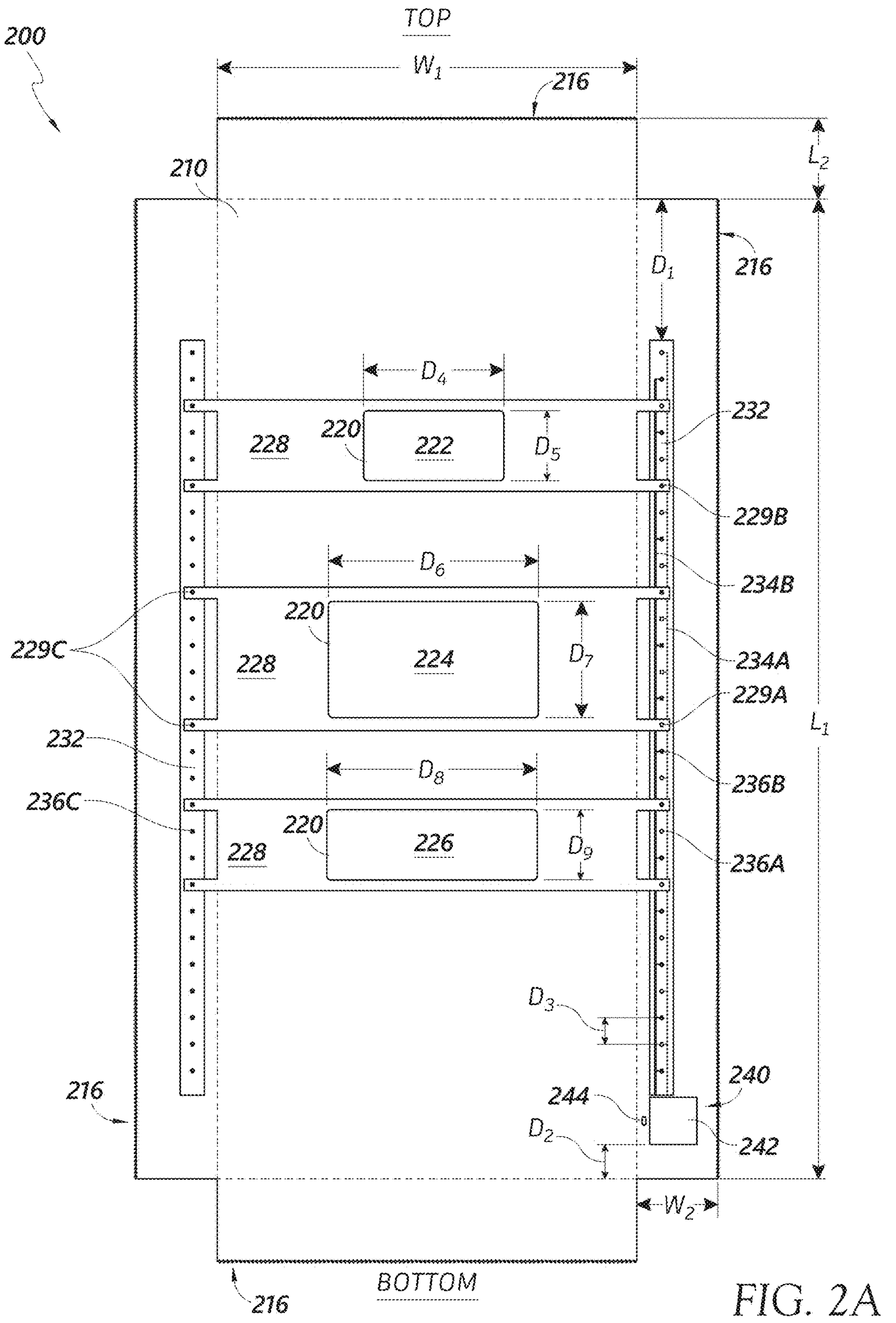
FIG. 2A illustrates an implementation of a stimulation system with removable electrodes.

In the illustrative and non-limiting example of FIG. 2A, the sheet 210 is a fitted hospital bedsheet. For this implementation, the sheet 210 has a width $W_1$ of approximately 91.5 cm (36") a length $L_1$ of approximately 213 cm (84") and pockets, such as corner pockets 112 of sheet 110, where $W_2$ and $L_2$ are each approximately 18 cm (7") to create a cover for a mattress thickness of up to approximately 18 cm (7"). As shown, the sheet 210 can be generally square or rectangular, but other shapes, such as straps or bands, trapezoids, circles, ovals, rings, notched rectangles, "T" shapes, donuts, horseshoes, dogbones, and other geometric or non-geometric shapes are also contemplated. Although particular dimensions and shapes are defined here, in general the sheet 110, 210 is not limited to those specific dimensions or shapes. The sheet 110, 210 can be any dimension, shape, or size for any covering of any surface 20 designed for, but not limited to, sitting or lying down.

In many implementations, the sheet 110, 210 is washable, moisture wicking, and shear and friction reducing. In some implementations, the sheet 110 is also stretchable and/or antimicrobial.

Electrodes

The electrodes 120 are designed specifically to deliver electrical stimulation to the patient 10 from the sheet 110, 210. Therefore, the electrodes 120 are placed on the sheet 110 in areas of the sheet 110, 210 that are most likely to contact high-pressure areas 12 on the skin of the patient 10. In some implementations, the sheet 110 is a fitted bedsheet that includes high-density padded, absorbent, and/or anti-microbial/antibacterial electrodes 120 embedded, releasably attached, or otherwise held strategically on areas of the sheet 110 most likely to contact the patient 10 in the most prevalent areas 12 in which pressure ulcers develop. In some implementations, the locations of the electrodes 120 correspond to the shoulder blades, elbows, and sacrum. For example, in some implementations, such as the sheet 110 of FIG. 1 and the sheet 210 of FIG. 2A, three electrodes 120, 220 correspond to the high-pressure regions 12, with a first electrode 222 for the scapulae, a second electrode 224 for the sacrum and trochanters, and a third electrode 226 for the ischial tuberosities. In some implementations, such as the sheet 270 of FIG. 2B, five shaped electrodes 280 have shapes and locations corresponding to these body locations, with a first electrode 282A for one scapula, a second electrode 282B for the other scapula, a third electrode 284 for the sacrum and two trochanters, a fourth electrode 286A for an ischial tuberosity, and a fifth electrode 286B for the other ischial tuberosity.

As illustrated in the various implementations, each of the anatomical targets can be contacted by an individual electrode or multiple electrodes 120, 220, (such as electrodes 282A and 282B for each scapula individually) or multiple targets grouped to a single electrode 120, 220. For example, in the illustrative implementation 210 of FIG. 2A, a mattress-cover type sheet 210 can include a first large electrode 222 corresponding to both shoulder blades, a second large electrode 224 corresponding to the two trochanters and sacrum, and a third large electrode 226 corresponding to the two ischial tuberosities. Electrode 222 has a width $D_4$ and height $D_5$ selected to contact both scapula (see FIG. 1). In this non-limiting example, the dimensions are approximately 30.5 cm by 15 cm (12" by 6") although other appropriate sizes are contemplated. Similarly, the width $D_6$ and height $D_7$ of electrode 224 are selected to contact both trochanters and the sacrum (e.g., approximately 51 cm by 25.5 cm or 18" by 10") and with width $D_8$ and height $D_9$ of electrode 226 are selected to contact both ischial tuberosities (e.g., 51 cm by 15 cm or 18" by 6") of the reclining patient. As with electrode 222, these dimensions are illustrative only, and are not intended to limit the size of the electrodes.

In some implementations, the sheet 110, 210, 270 can include distinct electrodes 120, 220, where each electrode corresponds to a single target. In some implementations, groups of electrodes 120, 220 can be activated together to cooperatively provide the electrical stimulation. For example, each shoulder blade area of a mattress sheet can include two or more electrodes 120, 220 (e.g., 2, 4, 5, 8, 16, or more electrodes). In some implementations, many electrodes are provided spaced across the entire sheet. For example, a bed sheet with 48 electrodes 120, 220 in a matrix can selectively activate a first set of electrodes 120, 220 under the patient where the skin is subjected to high pressure. A second set of electrodes 120, 220 can be activated near a different region of the skin to address a different localization of pressure, or the second set of electrodes 120, 220 can be activated in the same region of skin to compensate for movement of the patient 10 or changes in the pressure distribution. As shown, the electrodes 120, 220, 280 can be generally square or rectangular, but other shapes, such as strips or bands, trapezoids, circles, ovals, rings, notched rectangles, "T" shapes, donuts, horseshoes, dogbones, and other geometric or non-geometric shapes with optional rounded corners are also contemplated.

In some implementations, the electrodes 120, 220 are removable from the sheet 110, 210. In some implementations, the electrodes 120, 220 are integrated with the sheet 110, 210, 270. In some implementations, the sheet 110, 210 can include both removable and integrated electrodes 120, 220. Integrated electrodes 120, 220, 280 are machine-washable along with the sheet 110, 210, 270, and do not need replacement after use. Removable electrodes 120, 220 can be washable or disposable. In some implementations, removable electrodes 120, 220 are separately washable, while in other implementations the removable electrodes 120, 220 can remain attached to the sheet 110, 210 for laundering. In the illustrative implementation of the sheet 210 of FIG. 2A, the electrodes 222, 224, and 226 are washable as well as removable or repositionable. The electrodes 222, 224, and 226 are secured to an electrode housing pad 228, which includes fasteners 229 at each end. The housing pad 228 provides at least an electrical connection between the electrode 220 (e.g., 222) and the signal pathway 230 via one or more fasteners 229A and 229B. A mechanical connection can also be provided via fasteners 229C and/or fasteners 229A and 229B. In the illustrative embodiment of FIG. 2B, the electrodes 280 are integrated with the sheet 270 and the electrodes 280 are washed with sheet 270.

In some implementations, the fasteners 229A-C are half of a mating fastener set with fasteners 236A-C on the sheet 210. In some implementations, mating fasteners 229A-C and 236A-C are mating conductive snaps. For example, each housing pad 228 can be secured to the sheet 210 by connecting the mechanical fastener 229C to a mating fastener 236C on the sheet 210. Each housing pad 228 can also be electrically connected to the signal pathway 230 by connecting a positive electrical fastener 229A to a positive electrical line 234A with a mating positive electrical fastener 236A, and connecting a negative electrical fastener 229B to a negative electrical line 234B with a mating negative electrical fastener 236B. Further details of the signal pathway 230 are discussed below. Although the connections 229A-C and 236A-C are discussed above as being mating conductive snaps, other implementations include different suitable mechanical and electrical connections, such as conductive clips, hook-and-loop, pins, barrels, screws, lugs, and the like. This feature is discussed in further detail below, in association with the signal pathway 130, 230.

In many implementations, the electrodes 120, 220, 280 are designed to be washable, comfortable, moisture controlling, shear and friction reducing, and antimicrobial textiles. The electrodes 120, 220, 280 are electrically conductive to deliver the stimulation to the patient 10. In some implementations, the electrodes 120, 220, 280 include a layer of electrically conductive material. In some implementations, electrically conductive material is provided in or on other layers, such as the various layers discussed below. In some implementations, the electrodes 120, 220, 280 include absorbent material that draws in fluid and allows the electrode 120, 220, 280 to become conductive or more conductive. In some implementations, the electrodes 120, 220, 280 can include a gel, hydrogel, saline, or other electrolyte to enhance conductivity to the skin of the patient 10. In some implementations, the electrodes 120, 220, 280 are dry electrodes. Dry electrodes can be advantageous because they require little to no preparation to use effectively and the electrodes can be applied against hairy areas such as the back, legs, and scalp of the patient 10.

Figure 3:
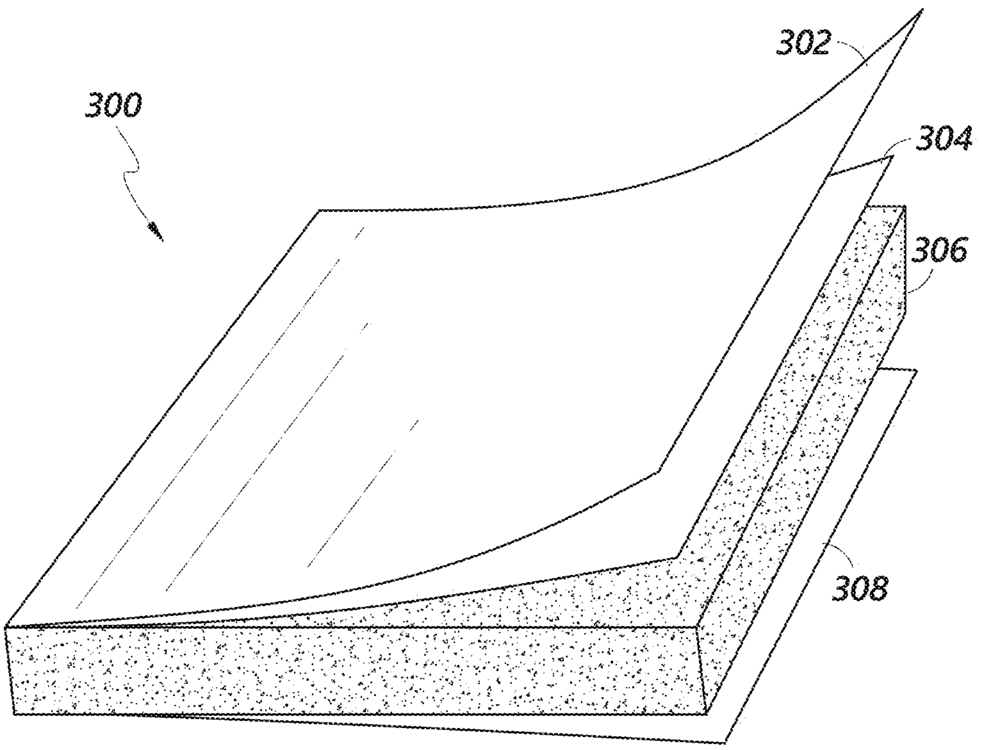
FIG. 3 illustrates a cross-section view of an implementation of an electrode of the stimulation sheet of FIGS. 1-2.

FIG. 3 illustrates one suitable type of dry electrode 300, which could be implemented in any of the electrodes 120, 220, 222, 224, 226, 280, 282A-B, 284, and/or 286A-B. A conductive layer 302 allows the stimulation signal to reach the patient 10. In some implementations, conductive layer 302 is a conductive textile or other flexible conductive material, such as conductive silicone. In some implementations, the conductive layer 302 is a conductive textile made from nylon and/or silk fibers embedded and/or woven with silver-plated polyurethane. The conductive layer 302 is connected to the signal pathway 130, as discussed below.

In some implementations the thickness of the electrodes 120, 220, 280, 300 creates a padded surface for the patient 10. The layering, size, and thickness of the electrodes 120, 220, 280, 300 can create a cushion for the patient 10, thereby reducing surface pressure and passively helping prevent pressure ulcer formation. In some implementations, the padding of the electrode 300 is provided by a padding layer, such as padding 306. In some implementations, the padding layer 306 is an elastic layer of a sponge having an appropriate thickness. In some implementations, the padding layer is 0.5 mm to 50 mm thick, preferably 1.0 mm to 20 mm, and more preferably 2.0 mm to 8 mm thick, depending upon the actual requirements. In some implementations, the padding layer 306 is an air layer, cellular fabric, or the like.

In some implementations, the padding layer 306 performs additional functions, such as moisture absorption or shear reduction as discussed below. In some implementations, the entire surface of electrode 300 is padded. In some implementations, only portions, such as a center portion or outer portion, are padded. In some implementations, the thickness of padding 306 is uniform, while in other implementations the thickness is non-uniform such as tapered or textured padding. Non-limiting examples of materials suitable for padding layer 306 include sponge, polyethylene (PE) and PE film, polyamide, polyester, silk, nylon, polyurethane, pure silver, and rubber.

Stagnant moisture is one of the factors towards the development of pressure ulcers and infection of open wounds. Therefore, in some preferrable implementations, breathable, absorbent, and/or wicking electrodes, such as electrode 300, can be used to control skin moisture and the electrode microclimate to help maintain skin integrity and prevent pressure ulcer formation. In some implementations the electrode 120, 300 is capable of absorbing moisture. In some implementations, the electrodes 300 include a wicking material, such as a wicking material in thin film layer 304. In some implementations, the electrodes 120, 300 are designed to absorb moisture, such as sweat, while remaining operable to deliver electrical stimulation signals to the patient 10. In some implementations, the electrodes 120, 300 are padded with absorbent or superabsorbent material, for example as padding layer 306. As mentioned above, some electrode implementations include wicking, absorbent, and/or superabsorbent materials that draw in fluid to allow the electrode to become conductive or more conductive. Non-limiting examples of wicking material include porous PE or PE film, cotton, hemp, rayon, microfibers, and the like. Non-limiting examples of absorbent and superabsorbent materials include sponge, PE, linen, cotton, terry, bamboo, and the like.

In many implementations, the electrodes 120, 300 are made of materials and/or laminates (e.g., in conductive layer 302 or in a body-contacting electrode cover) that reduce friction on the point of contact surface of the body of the patient 10. Such materials include, but are not limited to, nylon, silk, polyester, and combinations thereof. These materials, along with others like cotton, bamboo, and hemp, can be woven in satin, sateen, and the like to produce textiles that reduce friction on the point of contact surface of the body to lessen the likelihood of pressure ulcer formation. In some implementations of electrode 300, a nylon-silk surface 302 and rubber base backing 308 cooperate to decrease friction and shear, which is a cause of the formation of pressure ulcers.

In some implementations, pressure ulcer prevention can be facilitated by antimicrobial agents. These antimicrobial additives can be provided as a separate layer, or they can be embedded in any of the other electrode layers 302, 304, 306, 308. For example, in some implementations the electrodes 120, 300 can be embedded with threads, flaking, and/or microparticles of silver, copper, and/or the like. Some implementations can include antimicrobials selected to target particular infections. For example, electrodes 120, 300 can contain antiseptic, antifungal, or other agents selected to combat yeast, candidiasis or other mycosis, or other comorbid infections. In some implementations, antimicrobial agents can be included to specifically help treat existing pressure ulcers. For example, medicated gauze or other special dressings can be incorporated in or applied to the upper layer of the electrode 120, 300 to protect a wound and reduce further skin breakdown. The antimicrobial agents discussed here are non-limiting examples of materials selected to help prevent bacterial/microbial build up in the area in which wounds develop, thereby effecting the microclimate of the patient 10.

These various layers, materials, and functions can be combined to create a generally flexible and comfortable dry electrode 300 of the system 100. In one particular implementation, discussed here with reference to FIG. 3, the electrode 300 can include a conductive layer 302 made of woven nylon and/or silk embedded and/or woven with silver-plated polyurethane fibers for conductivity. This fabric is electrically conductive, anti-microbial, and shear-reducing. Thin film layer 304 is a film of polyethylene that helps the layers adhere together and provides a barrier to promote wicking of moisture (e.g., sweat) as discussed above. In this particular implementation, the thin film layer 304 cooperates with the padding layer 306 to draw and trap moisture. In this example, padding layer 306 is an elastic sponge material that provides cushioning and moisture absorption. Base layer 308 in this implementation is a non-conductive, non-slip rubber backing base cloth. The base layer 308 reduces the friction, and resulting electrical noise, caused by movement between the housing pad 208 and the underlying sheet 110, 210 when the patient 10 lies on the electrode 120, 300. The base layer 308 can function as the electrode housing pad 228, or it can be secured to a separate electrode housing pad 228. The laminated stack 302, 304, 306, and 308 cooperatively reduces shear applied to the patient by allowing the electrode 120, 300 to remain in place on the bed (via base layer 308) while the padding layer 306 deforms and the conductive layer 302 slides on the skin of the patient 10.

Figure 4:
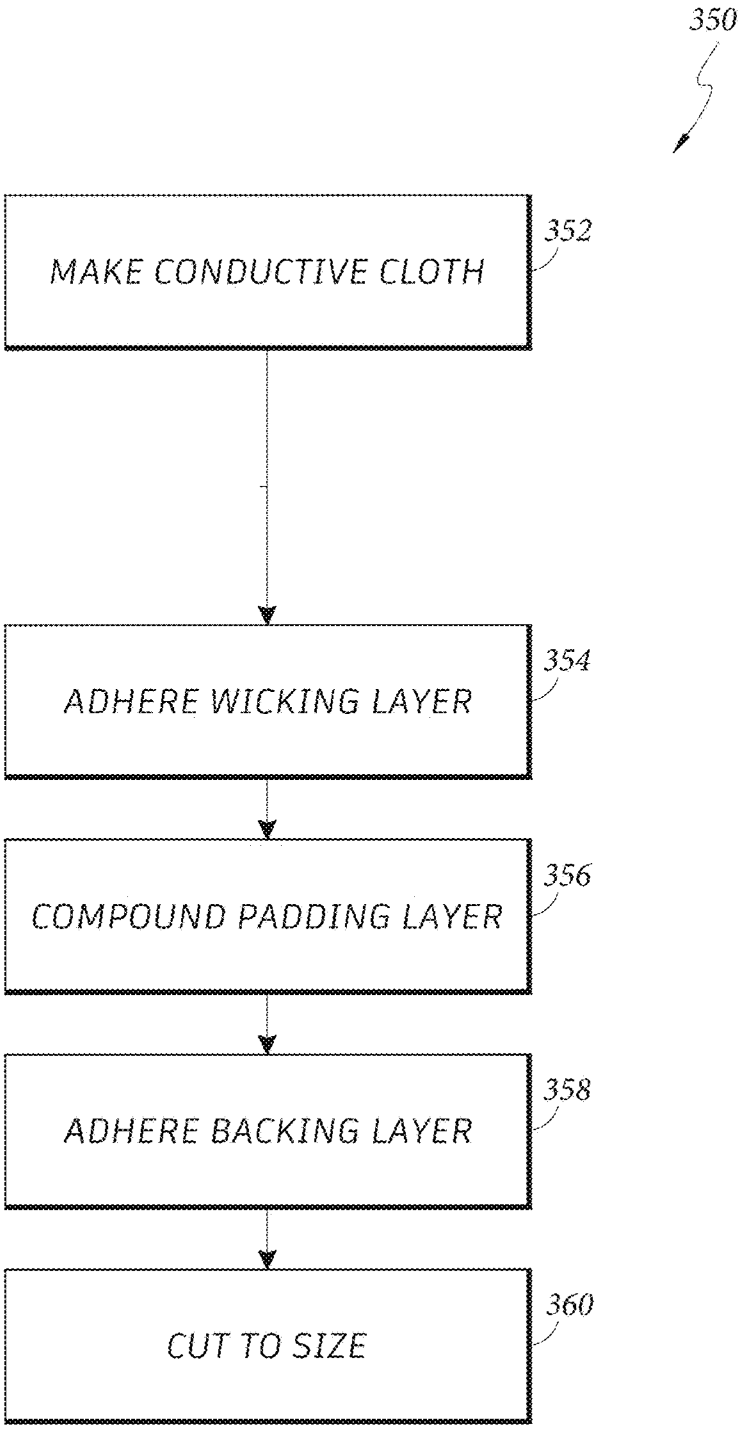
FIG. 4 illustrates an implementation of a method of manufacturing an electrode of the stimulation system.
Figure 5:
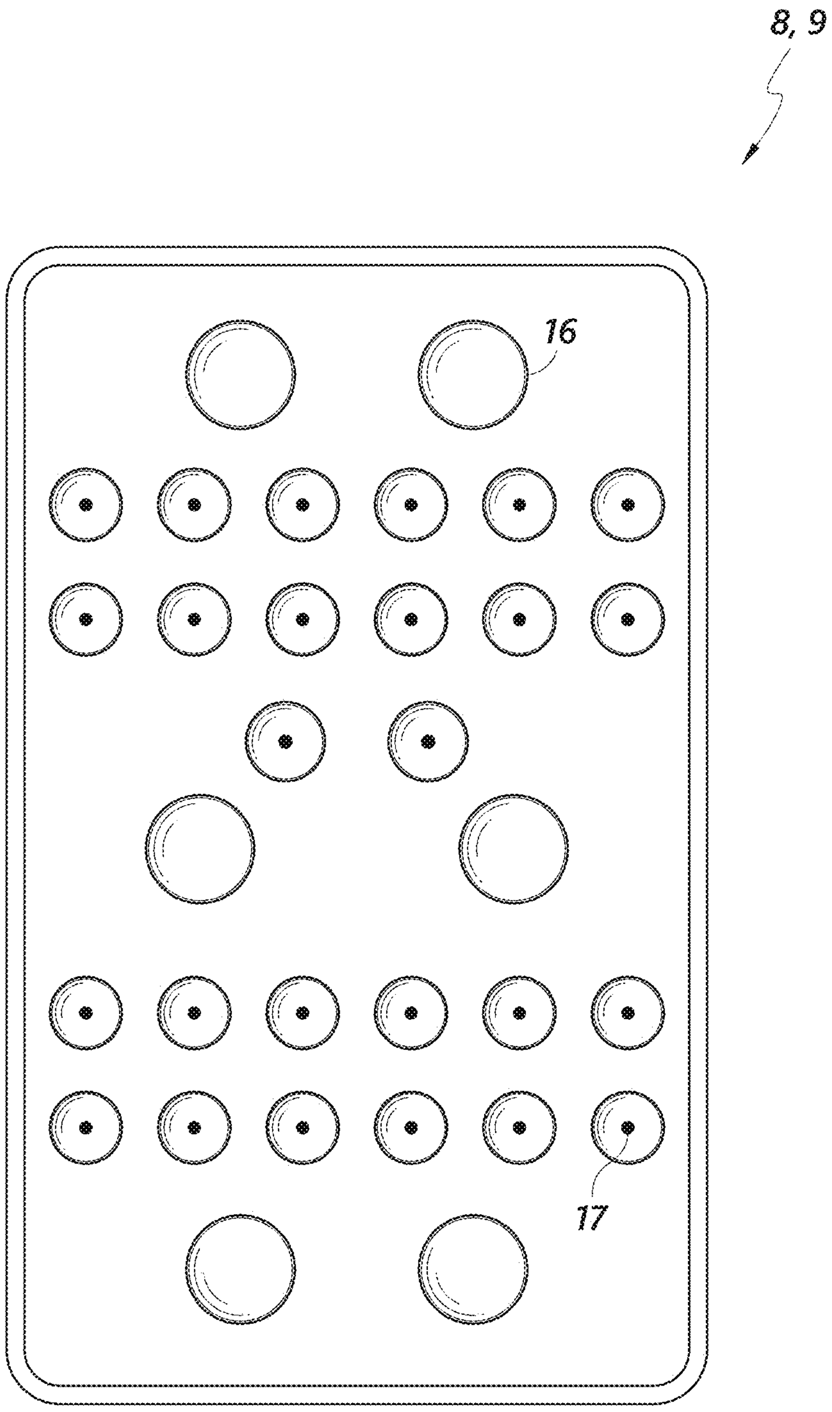
FIG. 5 illustrates an implementation of a magnetic control box connection for the stimulation sheet.

One example method of making close-fitting electrodes is illustrated in FIG. 4. Method 350 schematically shows the steps of making an electrode 300. The backing layer 308 is used for connection and fixed on an inner side of the interchangeable electrode housing pad 228, and the conductive layer 302 is fitted to the patient 10. In step 352, the conductive cloth is made. For example, in one implementation the conductive layer 302 is a conductive textile with silver plating for electrical conductivity. Elastic fabric (warp-knitted fabric, weft-knitted fabric or woven fabric) is woven from nylon/silk fiber and polyurethane. In some implementations, the nylon/silk fiber is a fine fiber. Chemical silver plating is performed on the clastic fabric to obtain a silver-plated cloth for conductive layer 302. In some implementations, the silver-plated cloth filaments can be twisted to ensure better elasticity. This implementation advantageously releases silver ions, which have a strong bactericidal effect. In some implementations, the silver-plated cloth of conductive layer 302 can be manufactured by any suitable method, such as a process in which silver is first plated on the surface of nylon/silk fiber that is then woven to form conductive elastic fabric. Another layer of silver may be plated onto the elastic.

In step 354, a thin film layer 304 is adhered onto the silver-plated cloth of the conductive layer 302 by dot-coating. In many implementations, the thin film layer 304 is a wicking film layer that can improve the absorption of sweat and allow moisture to quickly spread on the surface so that the electrical impedance is reduced quickly. In some implementations, the thin film layer 304 can also improve conductivity of the conductive layer 302 by pressing the silver particles of the conductive cloth together. This advantageously also reduces the loss of silver during washing and maintains good physical contact between the silver coils of the conductive textile 302, thereby improving washing durability.

In step 356, a padding layer 306 is compounded onto the thin film layer 304 by flame to obtain compounded electrode cloth. In some implementations, the padding layer 306 is an elastic/sponge layer that improves the fit of the electrodes to the skin of the patient. In step 358, the backing layer 308 is adhered. In some implementations, the backing layer 308 is a non-conductive rubberized base cloth that is compounded to the sponge of the padding layer 306. In some implementations, the base layer 308 is an elastic fabric layer or a laminate of elastic fabric and non-conductive rubberized cloth. Backing layer 308 can be compounded on the padding layer 306, such as a foam elastic padding layer 306, by dot-coating or by flame.

In step 360, the laminate electrode cloth obtained in steps 352-358 is cut according to the desired size to serve as the electrode 120, 220, 300. In some implementations, the conductive fabric 302 is cut in step 353, before being adhered to the thin film layer in step 354. In this case, the laminate stack may be cut or trimmed again in step 360, or the electrode may be considered finished after step 358. The obtained close-fitting electrodes have the characteristics of low resistivity, washing durability, uniform electrical conductivity, comfortable fitting effect and quick sweat absorption. Optionally, according to different requirements, a piece of mesh cloth may be adhered or compounded between the thin film 304 and the base layer 308. The mesh cloth can be included in addition to or instead of padding layer 306 in step 356.

Sensors

In addition to the electrodes 120, 220, 280, 300, the system 100 can optionally carry a variety of sensors 160. In some implementations, the system 100, 200 has one sensor 160. In some implementations, the system 100, 200 includes multiple sensors 160. In some implementations, the system 100, 200 has no sensors 160.

The sensors 160 used with various implementations of the system 100 are described herein, but are not limited to those explicitly discussed. Preferably, the sensors 160 include, but are not limited to, wet or dry electrodes, impedance sensors, pressure sensors, accelerometers, strain gauges, thermal sensors, pH sensors, hygrometers, chemical sensors, gas sensors, piezo sensors, photodetectors, magnetometers, static charge-sensitive beds, microphones, audio monitors, video monitors or cameras, actigraphs, and the like. Pressure sensors, temperature sensors, wetness detectors, pH sensors or sensors to sense or assess lack of circulation in an area, can be useful in preventing pressure ulcer formation. In most implementations, the sensors 160 are carried by the sheet 110, 210 and measure parameters of the patient 10. Sensors 160 can be built into or connected to the sheet 110, 210 in a manner similar to the stimulation electrodes 120, 220, 300 described above.

A variety of sensors 160 (e.g., biosensors) can be included in the system 100 for several purposes. For example, in some implementations, sensors 160 can be used to monitor biomarkers or physiological parameters of the patient 10. In some implementations, the sensors 160 are used to provide feedback (e.g., sense pressure and/or lack of circulation in an area and provides feedback). In some implementations, the feedback (e.g., alerts or indicators of deviations from expected parameters that are outside of a threshold range) is provided to the patient 10, a practitioner (e.g., clinician, medical professional, caregiver), and/or a remote location, such as a remote clinician, a medical record, and/or a monitoring station. In some implementations, the sensors 160 are used to adjust the stimulation provided by the electrodes 120, 220 (either automatically or in response to an adjustment command initiated by the patient or other person, e.g., health or medical practitioner or professional). For example, sensors 160 may sense pressure and/or lack of circulation in an area that triggers a correct amount of stimulation to be provided based on the sensing and continuously adjusts the stimulation based on the sensing over time. In accordance with several implementations, the sensors 160 advantageously provide diagnostic capability to an in-person or remote clinician or monitoring system. In accordance with several implementations, the system 100 facilitates diagnostic monitoring and/or intervention without requiring a patient 10 to be seen by a doctor or other provider in person. In other words, intervention may be provided via a telemedicine approach.

In some implementations, the sensors 160 are connected to the stimulation controller 150 but not placed on the sheet 110, and are arranged to measure parameters of the patient 10 or the environment. For example, a thermometer can be placed off the sheet 110 but near the patient 10 to measure the room temperature, or placed on the patient 10 on a body part not contacting the sheet 110 (for example, on a finger or the forehead) to measure body temperature. In some implementations, sensors 160 are located both on the sheet 110 and off the sheet 110 on and/or near the patient 10. In some implementations, the sensors 160 measure parameters of the room and patient 10 without being attached to the patient 10. Locating the sensors 160 in or on the sheet 110 and in the room can simplify use of the system 100 by avoiding complicated and time-consuming placement and connection of a sensor 160. Even so, as mentioned above some implementations include sensors 160 that are attached directly to the patient 10. For example, an accelerometer or actigraph can be attached directly to the limb(s) or torso of a patient 10 to detect movement or position and help predict the development of sustained pressure that would tend to cause or exacerbate a pressure ulcer.

Sensor 160 can include pressure sensors useful for directly measuring the pressure applied to the skin of the patient 10, which can be used to predict pressure ulcer formation. Such pressure sensors 160 can include any suitable sensor, such as piezoresistive pressure transducers, capacitive contact sensors, and impedance-based pressure sensors. These sensors 160 are generally, but not exclusively, located in or on the sheet 110 and placed to measure pressure applied to the skin of the patient 10. In some implementations, pressure is measured in the region of each electrode 120, 220. In some implementations, a pressure map of the entire surface of sheet 110, 210 is measured. In some implementations, the sheet 110 includes one pressure sensor 160. In some implementations, the sheet includes multiple pressure sensors 160 in different regions of interest.

In some implementations, sensors 160 are used to monitor the skin microclimate. As noted above, a warm and/or wet skin microclimate can lead to pressure ulcer formation. Additionally, one symptom of a Stage I pressure ulcer is increased local skin temperature resulting from the immune response of the patient 10. Therefore, increased local skin temperature can indicate formation of a pressure ulcer, or detect undesirable conditions that increase the likelihood of pressure ulcer development. Similarly, wetness and pH sensors are useful for monitoring the skin and electrode microclimates. In some implementations, a temperature sensor 160 can be used to monitor skin temperature and detect early pressure ulcer formation. In some implementations, a wetness sensor 160 can indicate that the skin is too dry (e.g., chapped or burned) or too wet. In some implementations, an impedance sensor 160 is used to measure contact between an electrode 120 and the patient 10, pressure applied to the skin, edema, and/or skin breakdown. In some implementations, these sensors 160 provide signals indicative of pressure ulcer formation, or conditions that would tend to cause pressure ulcer formation. In some implementations, the indicative signals can be used to alert the patient 10 or a caregiver that the patient 10, surface 20, sheet 110, stimulation electrode 120, and/or sensor 160 needs to be adjusted. In some implementations, such adjustments can include reconnecting, relocating or repositioning, removing, washing, or replacing.

In some implementations, the sensor parameter is continuously measured. In some implementations, the parameter is periodically sampled. In some implementations, the parameter is periodically sampled while the measurements are below a predetermined threshold, and continuously monitored if the measurement is above the threshold. For example, skin pressure may be monitored hourly while the pressure measurement is under a threshold or the skin temperature is within a predetermined range.

In some implementations, the sensors 160 are removable from the sheet 110. In some implementations, the sensors 160 are integrated with the sheet 110. In some implementations, a sheet 110 can include both removable and integrated sensors 160. Integrated sensors 160 are machine-washable along with the sheet 110, and do not need replacement after use. Removable sensors 160 can be washable or disposable.

Signal Pathway and Connections

The system 100 includes a signal pathway 130 to connect the various components. In some implementations, the signal pathway 130 allows two-way communication between the components, while in other implementations the communication is limited to one direction. In some implementations, the delivered signals are data and/or power. For example, in an implementation including sensors 160 as discussed above, the signal pathway 130 can deliver stimulation signals from the stimulation controller 150 in control box 152 to the stimulation electrodes 110, power from the control box 152 to a sensor 160, and sensor signals from the sensor 160 to the control box 152.

In most implementations, the electrical current is transmitted through a physical signal pathway 130 in or on the sheet 110. In some implementations, the signal pathway 130 is a washable electrically conductive cabling, threading, ink, or other conductive pathway. In some implementations, the signal pathway 130 is sewn or placed on or within the sheet 110. Preferably, the signal pathway 130 is machine washable with the sheet 110. In some implementations, the signal pathway 130 is removable from the sheet 110, to allow the sheet 110 and/or electrodes 120 to be laundered. In some implementations the signal pathway 130 is elastic or stretchable (e.g., serpentine).

For some implementations, preparing an elastic signal pathway 130 is similar to preparing the conductive cloth of some of the electrodes, such as electrode 300 discussed above. For example, an elastic and washable signal pathway 130 can be formed by plating chemical silver on nylon/silk fiber to form a conductive silver-plated nylon silk fiber. A plurality of these conductive silver-plated nylon/silk fiber filaments can be twisted and merged with polyurethane. In some implementations, a signal pathway 130 with long wiring has a consistent length resistivity of 18 to 20 Ω/m. For many implementations, the necessary size of the signal pathway 130 is 1.10 m or less. Therefore, all leads of the signal pathway 130 can be controlled below 30Ω. This feature allows the wiring of the signal pathway 130 to have low energy consumption and increase the battery life of a portable device. This construction also withstands multiple washings, and maintains performance because the loss of silver is low.

In some implementations, the signal pathway 130 includes a connection for each component, such as electrodes 120, sensors 160, and stimulation controller 150. In some implementations, the signal pathway 130 alternatively or additionally includes a bus or rail, to which each component is connected. In some implementations, some or all components are permanently connected to the signal pathway 130. For example, the sheets 110 with embedded electrodes 120 and/or sensors 160 as described above have stimulation electrodes 120 and sensors 160 permanently connected to the signal pathway 130. In some implementations, the components are attached with releasable connections. For example, the stimulation electrodes 120 and/or sensors 160 can be releasably connected to the signal pathway 130 via snap, clip, magnet, or other connector. In some implementations, the electrode 120 and/or sensor 160 can be permanently or releasably connected via adapter to make a suitable electrical connection.

In the representative implementation illustrated in FIG. 2A, the signal pathway 130 also functions to hold the electrodes 222, 224, and 226 in place. As discussed above, the electrode housing pad 228 includes fasteners 229A-C that secure to mating fasteners 236A-C on a fastener support material 232. Fastener support material 232 can include spaced fasteners 236C that mate with fasteners 229C on the electrode backing 228 to mechanically secure the electrode backing 228, and thereby each electrode 220, to the sheet 220. Each sheet 220 can include multiple fastener support materials 232 and associated sets of fasteners 236. As discussed below, fasteners 236 can include positive terminal fasteners 236A, negative terminal fasteners 236B, and/or neutral or disconnected fasteners 236C that are grounded or have no electrical connection.

Fastener support material 232 also carries a positive connection line 234A and a negative connection line 234B. The positive connection line 234A includes positive connection terminals 236A that mate with the electrode fasteners 229A. Similarly, the negative connection line 234B includes negative connection terminals 236B that mate with the electrode fasteners 229B. In some implementations, the positive connection line 234A and negative connection line 234B are bundles of wires, each wire connecting the stimulation controller connection 244 to one of the terminals 236A or 236B, respectively. In some implementations, the positive connection line 234A and negative connection line 234B operate as a bus with multiple positive connection terminals 236A and negative connection terminals 236B. In some implementations, the positive connection line 234A is made of individual wires for each electrode 220, and the negative connection line 234B is a single negative (return or ground) line for all electrodes 220. These examples are not limiting, and other combinations of shared and discrete wires are contemplated.

In some implementations, such as that of FIG. 2A, the terminals 236A and 236B are interleaved or alternating, and are located at a known distance. For example, spacing distance $D_3$ between each terminal can be 5 cm (2") where the terminals are evenly spaced along the side of the sheet 110, 210 as in FIGS. 1-2. In these implementations, the negative terminals 236B are spaced every 10 cm (4") and the positive terminals 236A are also spaced every 10 cm (4") to allow the connected electrodes 222, 224, 226 to be placed at an appropriate location along the length $L_1$ of the sheet 210. In some implementations, the signal pathway 230 in the fastener support material 232 begins a distance $D_1$ from the head of the bed and extends to an end that is a distance $D_2$ from the foot of the bed. In some implementations, the distance $D_1$ is approximately 30.5 cm (12") and the distance $D_2$ is approximately 8 cm (3") to span the majority of the length $L_1$ of the sheet 110. These locations are illustrative only, and can be adjusted as appropriate for other implementations to locate the electrodes 220 in particular areas of interest. In some implementations, terminals 236C are located at the same spacing distances.

Figure 2B:
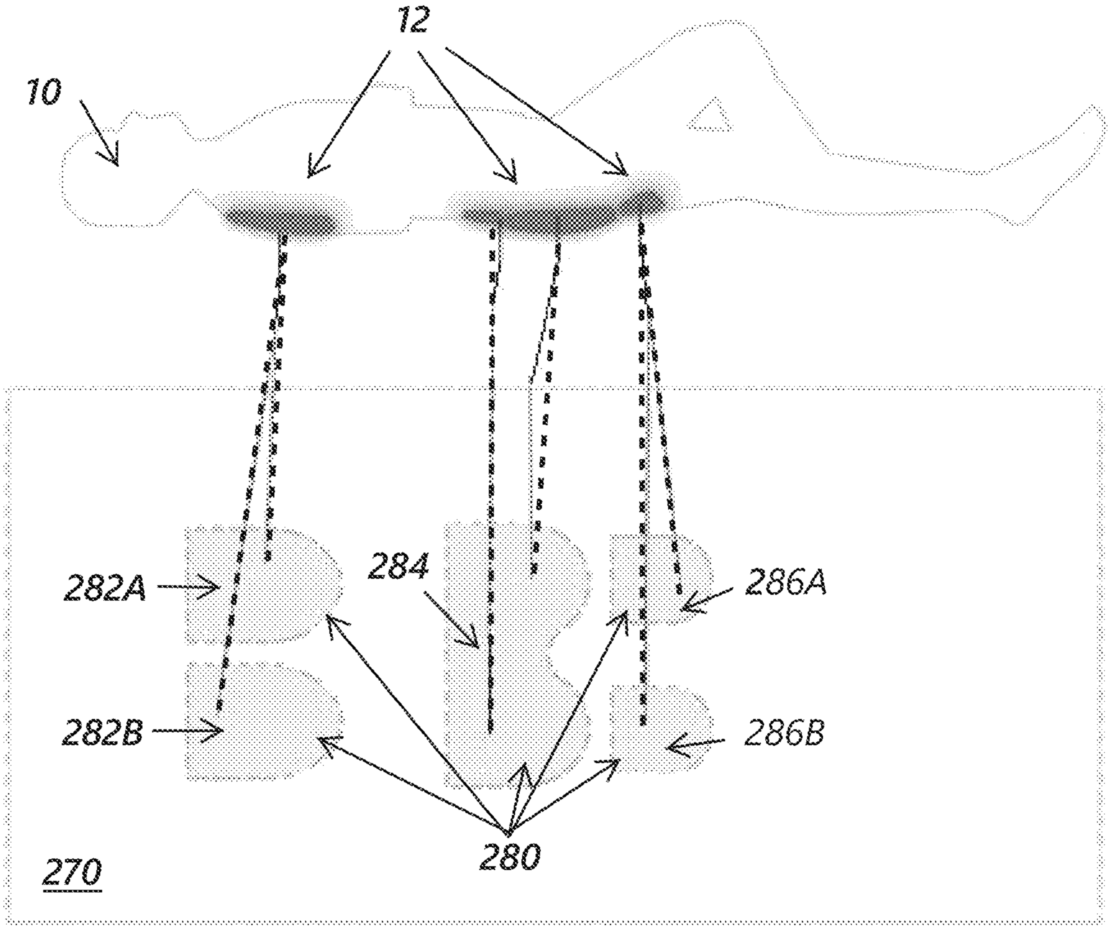
FIG. 2B illustrates an implementation of a stimulation system with integrated and shaped electrodes.

In the example implementation of FIG. 2B, the electrodes 280 are integral with the sheet 270. The signal pathway (not shown) can be similar to the signal pathways 130, 230 discussed above in some or all respects. The signal pathway can also be washable conductor(s) integrated or embedded with the sheet 270, or a removable structure such as a wiring harness with conductive connections for electrodes 120, 220, 280, any sensors 160, and/or a control box 150, 250.

At least one end of the signal pathway 130, 230 terminates at a controller connection area 140, 240, where the signal pathway 130, 230 connects to at least a stimulation controller 150 in a control box 152. The controller connection area 240 includes a mechanical connection 242 and an electrical connection 244. The mechanical connection 242 holds the control box 152 in place on the sheet 110, 210. The electrical connection 244 electrically connects the stimulation controller 250 to the electrodes 120, 220. The electrical connection 244 can also provide an electrical connection 244 to any optional sensors 160, and may also provide the mechanical connection 242 and/or an additional mechanical connection 242. In some implementations, the controller connection area 240 includes a magnet plate. In some implementations, the controller connection area 240 is a rail or clip to provide both mechanical connection 242 and electrical connections 244. In some implementations, the controller connection area 240 is a plug or clip for an electrical connection 244, and the mechanical connection 242 is provided separately. In some implementations, the separate mechanical connection 242 is, or is within, a pocket as shown in FIGS. 1-2. In some implementations, the mechanical connection 242 is a strap or band of elastic, hook-and-loop, buckle, drawstring, clip, shelf, and the like. In some implementations, the controller connection area 140, 240 includes an adapter.

In some implementations, such as the examples illustrated in FIGS. 5-12, the controller connection area 140 on the sheet 110 provides both a mechanical and electrical connection. As shown in FIG. 6A, the connector 1200 includes an interior portion with an inner or bottom plate 1222 and an interior or lower printed circuit board (PCB) 1206. An exterior portion includes a reinforced outer or upper plate 1202, an external cover 1201, and an exterior PCB 1210.

Outer plate 1202 in this example is a reinforced acrylonitrile butadiene styrene ("ABS") plate. In some implementations, the outer plate 1202 is a shaped rail, for example a T-shaped rail. In some implementations, the outer plate 1202 is a smooth or textured skid plate. The outer plate 1202 can help align the electrical connectors, provide mechanical stability for the connection, and improve durability of the sheet 110. The outer plate 1202 includes a cover 1201 that protects and secures the electrical connector 1216 and the associated outer PCB 1210. In some implementations, the cover 1201 is shaped to provide a mechanical connection 242 for the control box 152, thereby helping secure the control box 152 when the control box 152 is connected to the connection area 140, 240. The outer plate 1202 also includes a clip 1232 that fits into a mating slot 1242 in the inner plate 1222 to secure the end of the outer plate 1202.

Inner plate 1222 can be made of similar acrylonitrile-butadiene-styrene (ABS) plastic or another plastic or polymeric material. In some implementations, the inner plate 1222 is made of the same material as outer plate 1202. In some implementations, the inner plate 1222 is made of a different material, for example a more flexible material. In some implementations, the inner plate 1222 includes an opening or recess for the inner PCB, such as PCB 1206. The space can include a support 1208 to hold the inner PCB 1206.

Figure 6A:
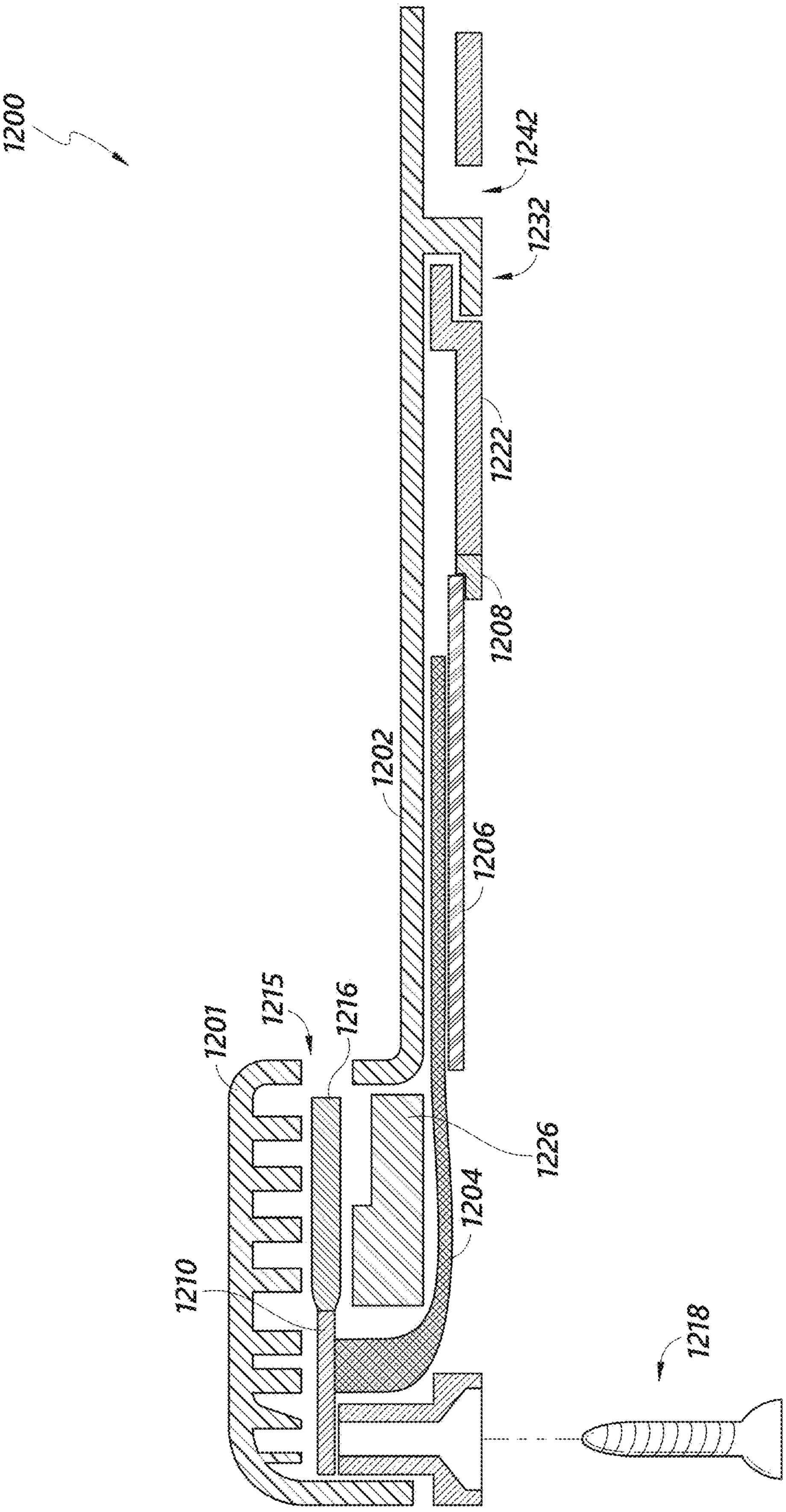
FIG. 6A illustrates a section view of an implementation of an electromechanical control box connection for the sheet.
Figure 6B:
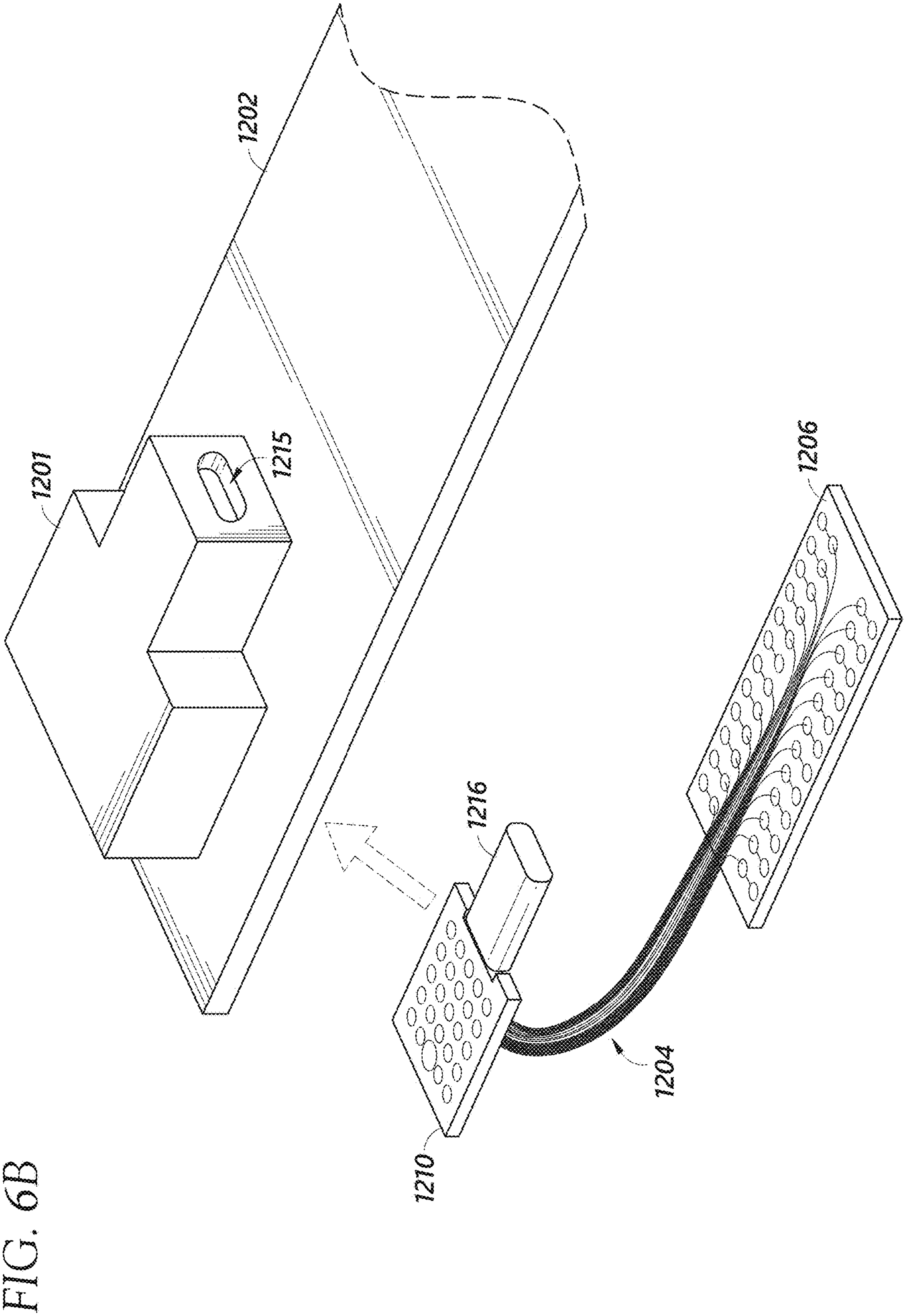
FIG. 6B illustrates an exploded view of a portion of the implementation of the control box connection of FIG. 6A

The inner plate 1222 can also include a housing 1226 for routing, containing, and protecting the wires, such as wires 1204 and outer PCB, such as PCB 1210. Housing 1226 includes a cavity for holding the outer PCB and a recess 1215 for the connector, such as connector 1216. In some implementations, the housing 1226 extends outward from the inner plate 1222 to connect with the mating housing, for example cover 1201, of the outer plate 1202. In some implementations, the cover 1201 of outer plate 1202 extends inward to mate with housing 1226 of outer plate 1202. In some implementations, the mating housings 1201/1226 both extend toward each other, as illustrated in FIG. 6A. The cover 1201 and housing 1226 individually or cooperatively form opening 1215 to allow protected access to the connector 1216.

Part of the housing 1226 can further include a through-hole, for securing the inner plate 1222 to the outer plate 1202, for example with screw 1218 or other fastener. In addition to the screw attachment 1218, the inner plate 1222 can include slot 1242, to mate with a clip 1232 and secure the end of the plates 1202 and 1222 together.

Figure 7:
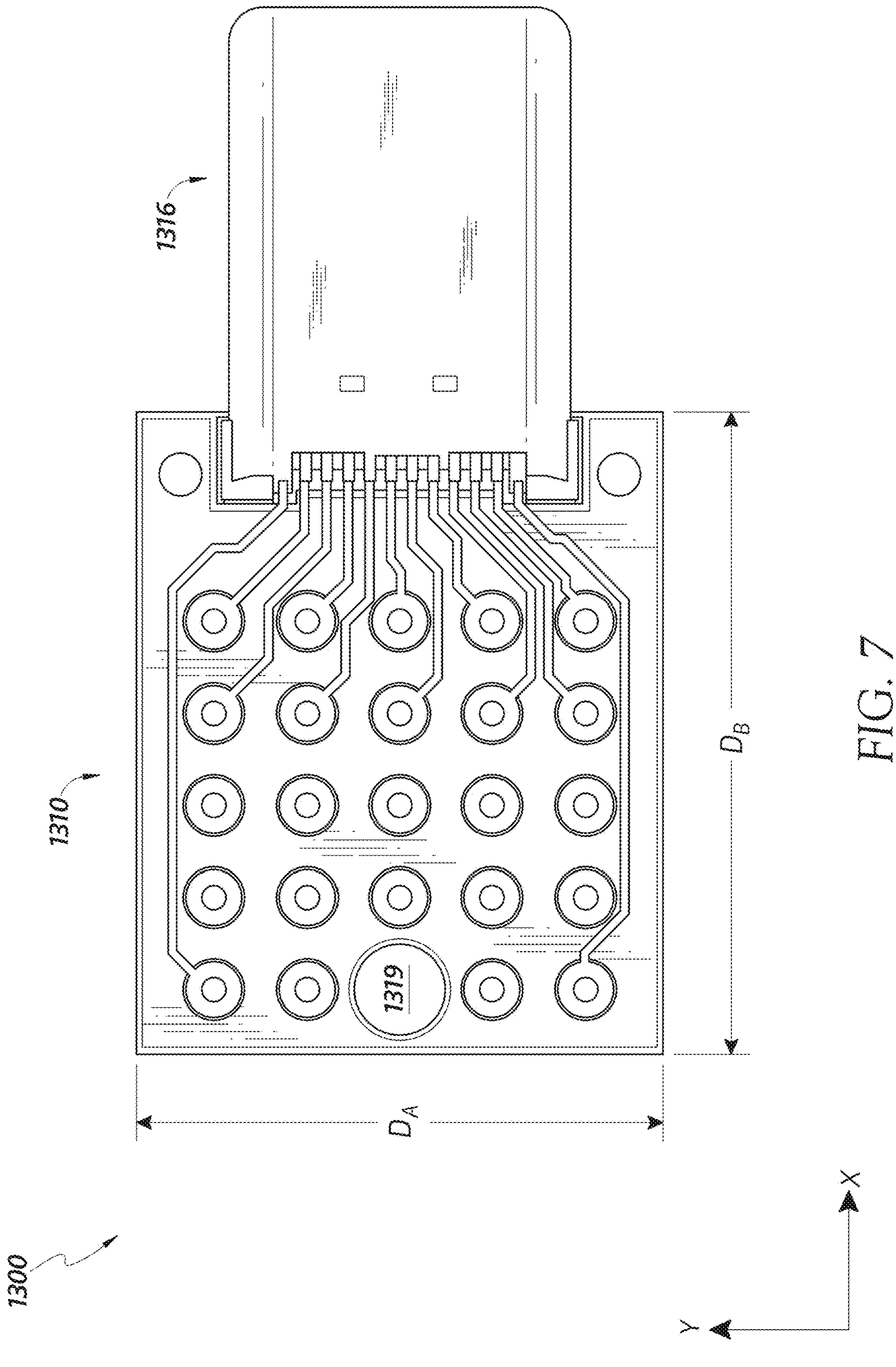
FIG. 7 illustrates an implementation of an outer printed circuit board of the control box connection of FIGS. 6A-B.
Figure 8A:
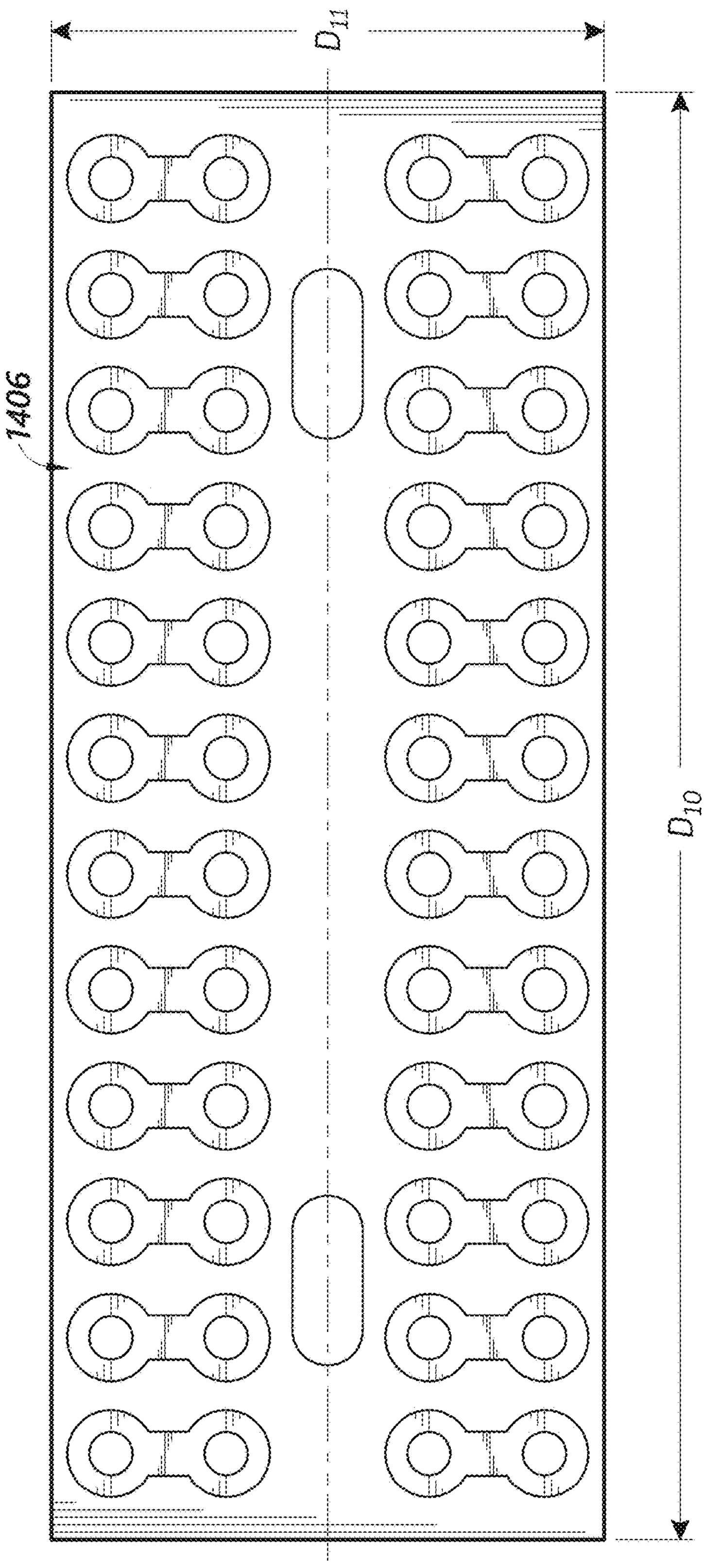
FIGS. 8A and 8B illustrate top and side views of an implementation of an inner printed circuit board of the control box connection of FIGS. 6A-B.
Figure 8B:
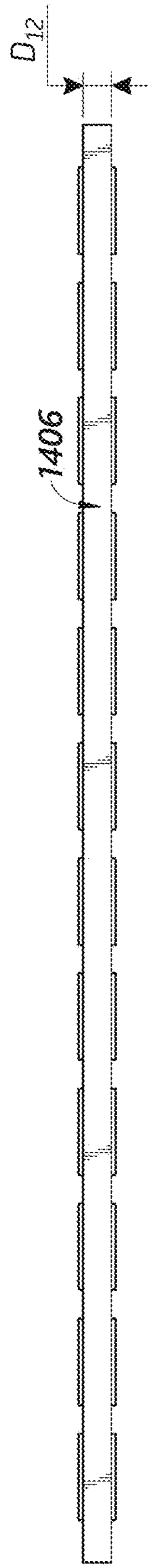

The electrical connector 1216 is attached to the external PCB 1210. FIG. 7 illustrates one example assembly 1300 including the external PCB 1210. In example assembly 1300, USB-C connector 1316 connects to the board 1310. In this example, the external PCB 1310 has dimensions $D_A$ and $D_B$ of 12.4 mm and 15.2 mm respectively, although any suitable dimensions can be selected as appropriate.

The external board 1310 can include a through-hole 1319 to align and secure the board 1310 in place inside the housing. For example, a fastener, such as screw 1218, optionally fits through hole 1319 to hold outer board 1310 in place under the cover 1201.

The interior PCB 1206 is connected to the exterior PCB 1210 via flexible wires 1204. In some implementations, the inner PCB (e.g., 1206) includes twenty-four connections, as illustrated in example inner PCB 1406 of FIG. 8A. In some implementations, the inner PCB 1206 is a two-sided board, as shown in example inner PCB 1406 of FIGS. 8A-B. The example implementation of FIGS. 8A-14B, inner PCB 1406 has dimensions $D_{10}$ and $D_{11}$ of 50.0 mm and 19.0 mm, respectively, and a thickness $D_{12}$ of 1.0 mm. In some implementations, the inner PCB size, number of connections, and layout can vary as appropriate. For example, on sheets 110, 210 with a small number of electrodes 120, 220 and/or sensors 160, the inner PCB can be smaller, such as the length $D_{10}$ of 25 mm and twelve double-sided connections, or a width $D_{11}$ of 10 cm and a length $D_{11}$ of 50 mm with twelve single-sided connections. In some implementations, the inner PCB includes the same twenty-four double-sided connections on the same size board as inner PCB 1406 of FIG. 8A, but some connections are not used.

Figure 9:
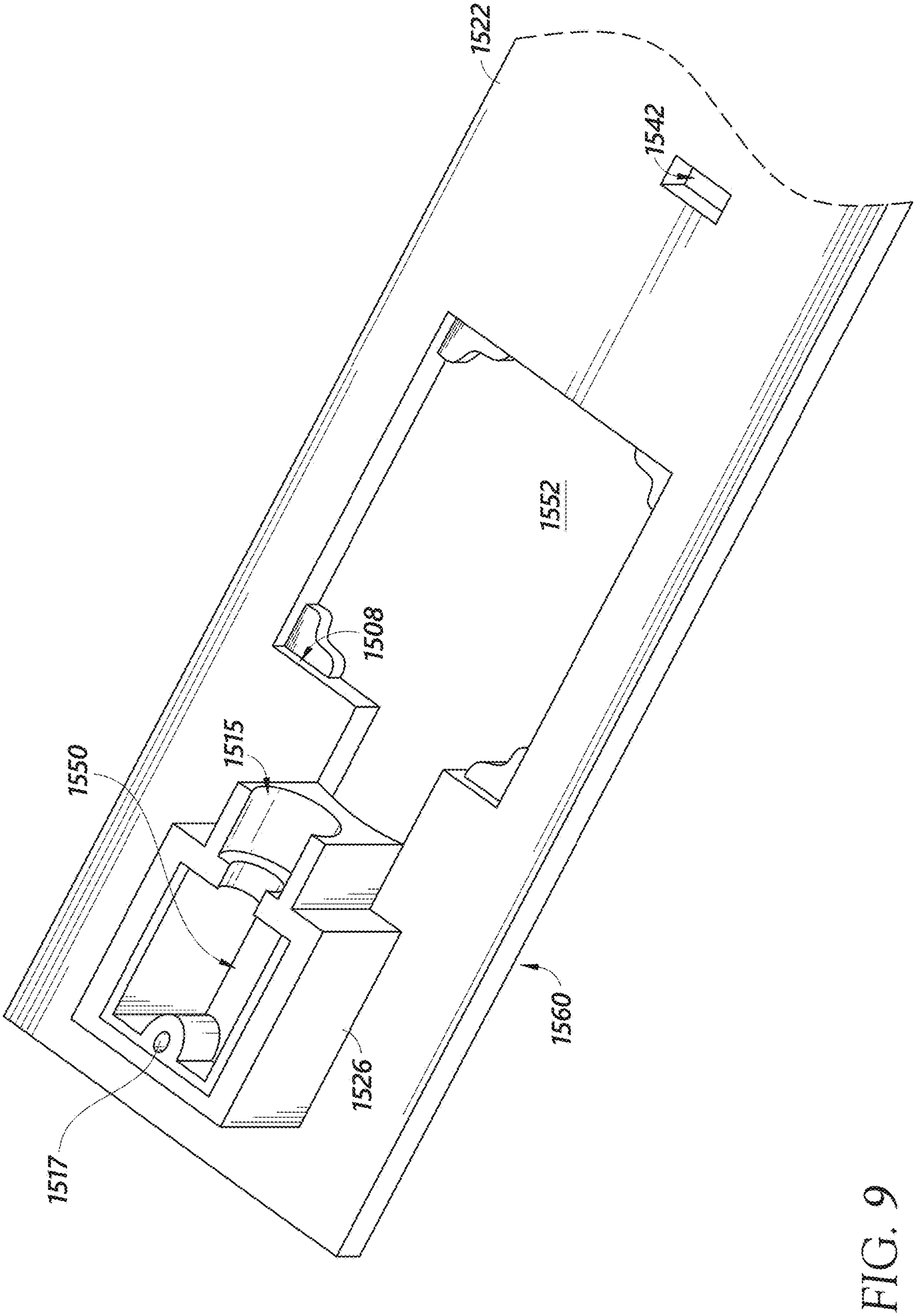
FIG. 9 illustrates an implementation of an inner plate of the control box connection of FIGS. 6A-6B.

FIG. 9 illustrates another implementation of an inner or lower plate of a controller connection area 140. Various elements of inner plate 1522 can be the same as or similar to the lower plate 1222 in some or all respects. For example, inner plate 1522 can include a slot 1542 similar to slot 1242 that mates with clip 1232. Inner plate 1522 can also include an opening or recess 1552 for an inner PCB, such as PCB 1206 or 1406. The opening 1552 can optionally include a clip or notch 1508, similar to support 1208, to hold the inner PCB 1206, 1406. The inner plate 1522 can also include a housing 1526 for routing, containing, and protecting the wires, such as wires 1204, and an outer PCB, such as PCB 1210 or 1310. As illustrated, housing 1526 can include a cavity 1550 for holding the outer PCB and a recess 1515 for the connector, such as connector 1216. Housing 1526 can further include at least one hole 1517 to help secure inner plate 1522 to an outer plate, for example outer plate 1202. Hole 1517 can be used to hold a mating alignment pin, a screw (such as screw 1218), or other fastener. In accordance with several implementations, the thickness 1560 of the inner plate 1522 is small so the inner plate 1522 is sufficiently flexible. For example, the thickness 1560 can be approximately 2 mm, although other dimensions are also suitable, depending on the desired levels of rigidity, comfort, and materials.

Figure 10A:
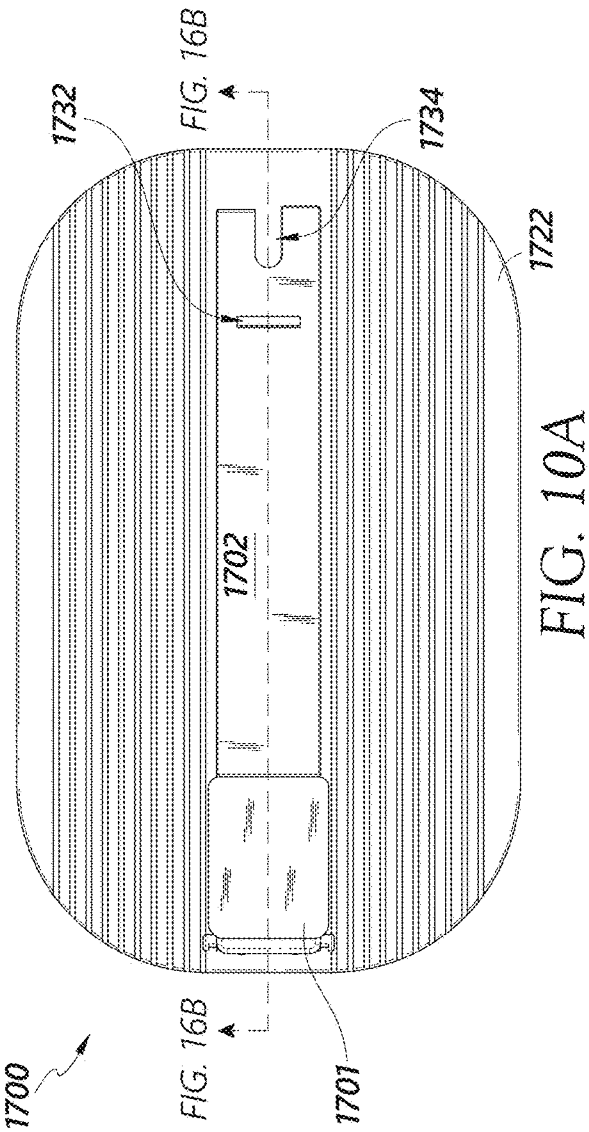
FIGS. 10A, 10B, and 10C illustrate another implementation of a control box connection between the sheet and the control box.
Figure 10B:
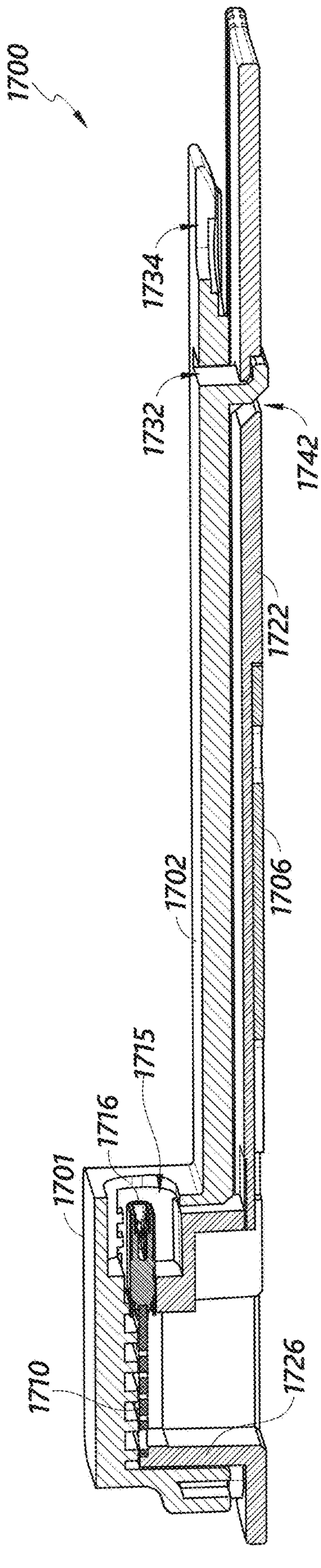
Figure 10C:
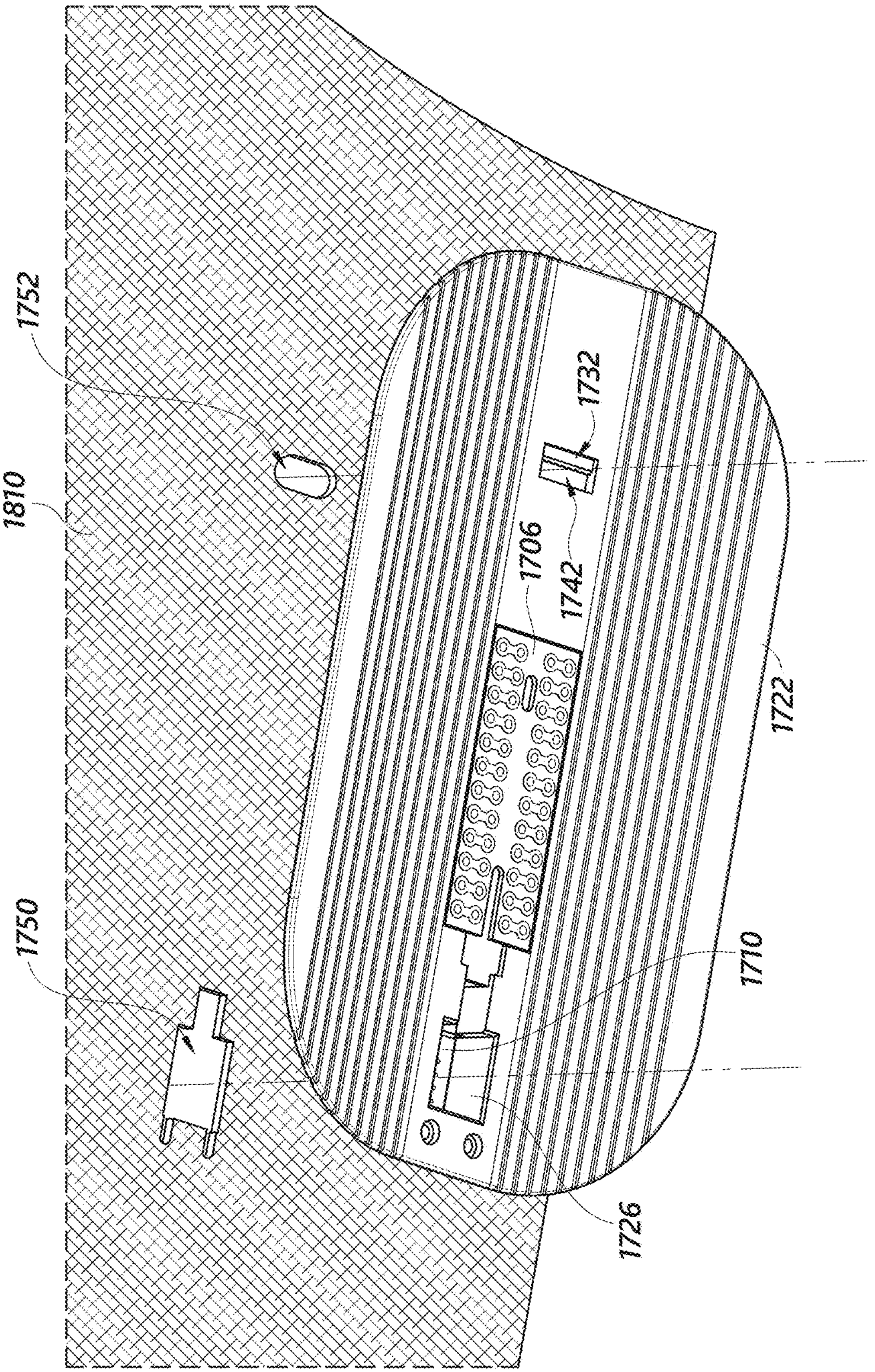

FIGS. 10A to 12B illustrate another implementation 1700 of connection area 140 of sheet 110, 210. Various elements of connection 1700 can be the same or similar to the connection elements of FIGS. 6-9 in some or all respects. FIG. 10A illustrates a top or external view of a portion of the connection 1700, and FIG. 10B shows a sectional view taken along line FIG. 10B-FIG. 10B. A bottom or internal view of the same connection 1700 is illustrated in FIG. 10C.

Outer plate 1702, including clip 1732, opening 1715, and cover 1701 can be similar to outer plate 1202, including clip 1232, opening 1215, and cover 1201. Outer plate 1702 can also include securing groove 1734 to optionally mate with a retention pin on the back of a control box 122. Internal circuit board 1706, external circuit board 1710 with electrical connector 1716, and the connecting wires (not shown) can be similar to internal circuit board 1206 or 1406, external circuit board 1210 or 1310 with electrical connector 1216 or 1316, and connecting wires 1204.

Inner plate 1722, including retention slot 1742 and housing 1726 can be similar to inner plate 1222 with retention slot 1242 and housing 1226. Clip 1732 can releasably snap into slot 1742 through hole 1752 in suit 1810. The clip 1732 and slot 1742 cooperate to secure outer plate 1702 to inner plate 1702 and sandwich the circuit boards 1706 and 1710 and the suit 1810 in place. Housing 1726 of the inner plate 1722 and cover 1701 of the outer plate 1702 mate to enclose the external circuit board 1710 and electrical connector 1716. The mating housing 1726 and cover 1710 cooperate to protect the circuitry (e.g., internal circuit board 1706, external circuit board 1710, and the connecting wires) as they cross from inside the suit 1810 to outside the suit 1810 through hole 1750.

As above, housing 1726 and cover 1701 may individually or collectively form opening 1715 to access the electrical connector 1716. In the illustrative connector 1700, cover 1701 forms the opening 1715. The housings 1726 and cover 1701 can be nested or partially nested. For example, cover 1710 fits over at least a portion of housing 1726. The cover 1710 and housing 1726 can be held with a screw, such as screw 1218, or other means of securing the parts, such as friction fit, clip, pin, adhesive, and/or other suitable connector(s). In some implementations, multiple pins, clips, and/or screws can secure the housing 1726 and cover 1710. As above, in some implementations, external circuit board 1710 can include a through-hole (such as hole 1319) for securing and/or aligning the board 1710.

Figure 11A:
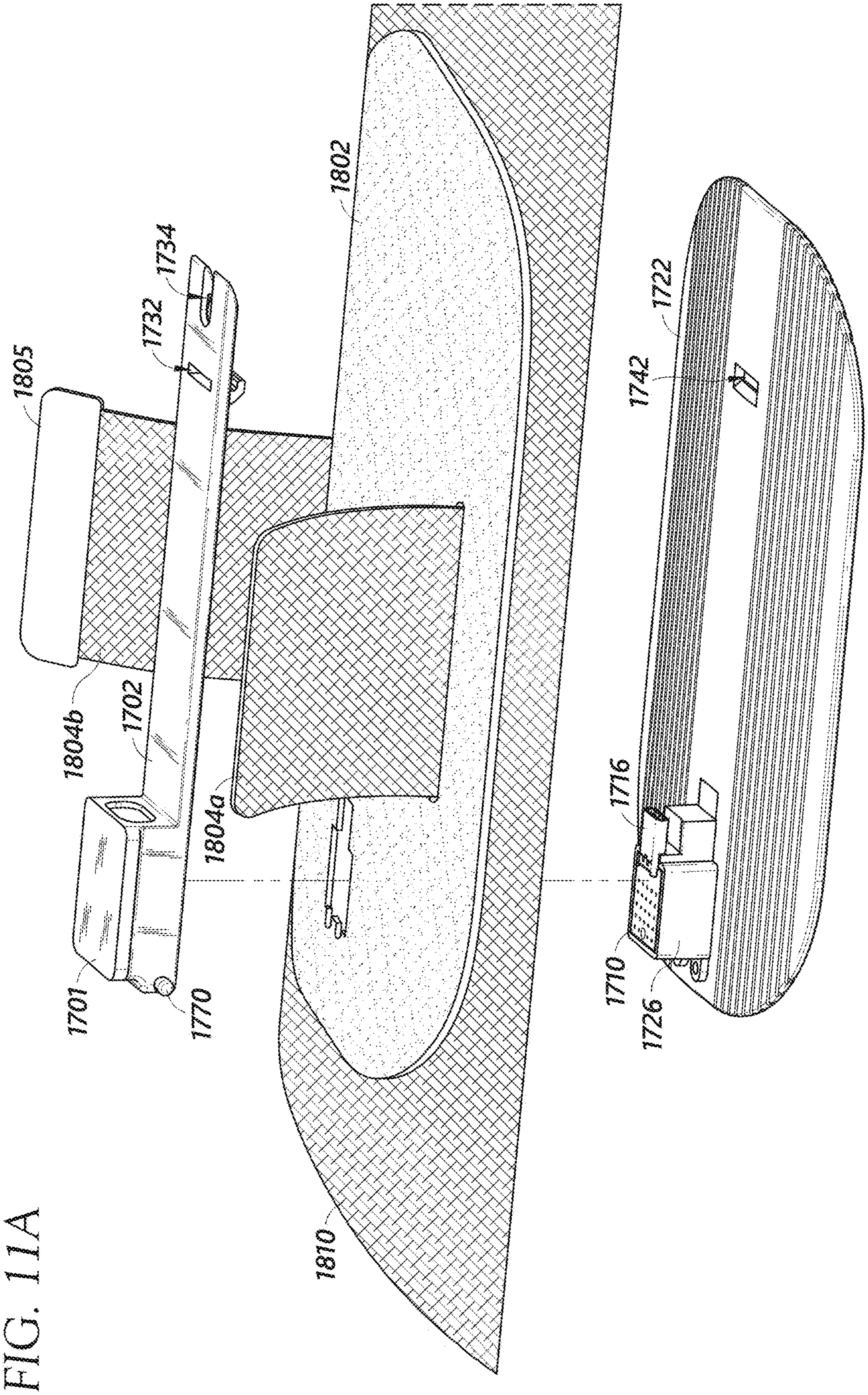
FIGS. 11A, 11B, and 11C illustrate another implementation of a control box connection between the sheet and the control box.
Figure 11B:
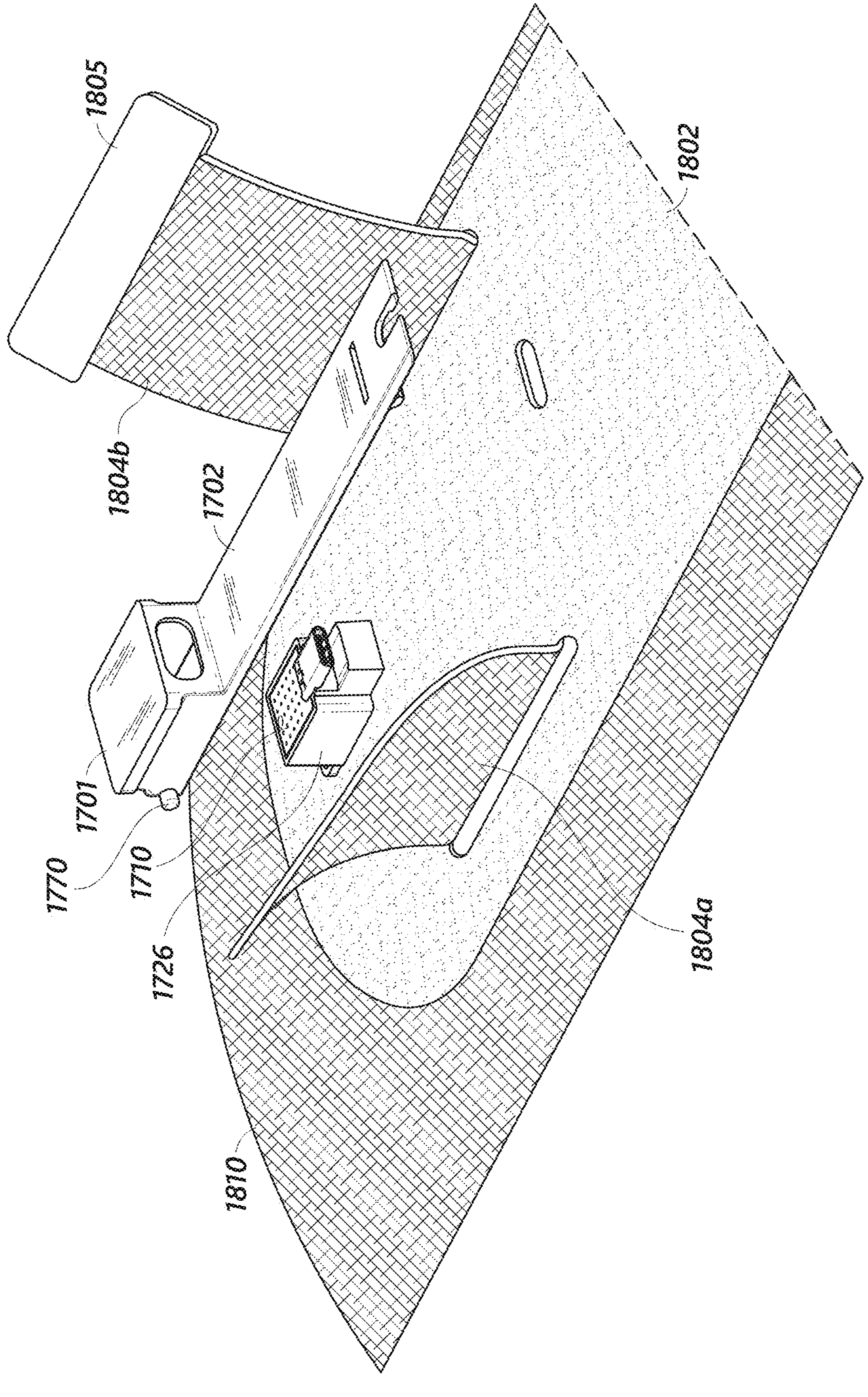
Figure 11C:
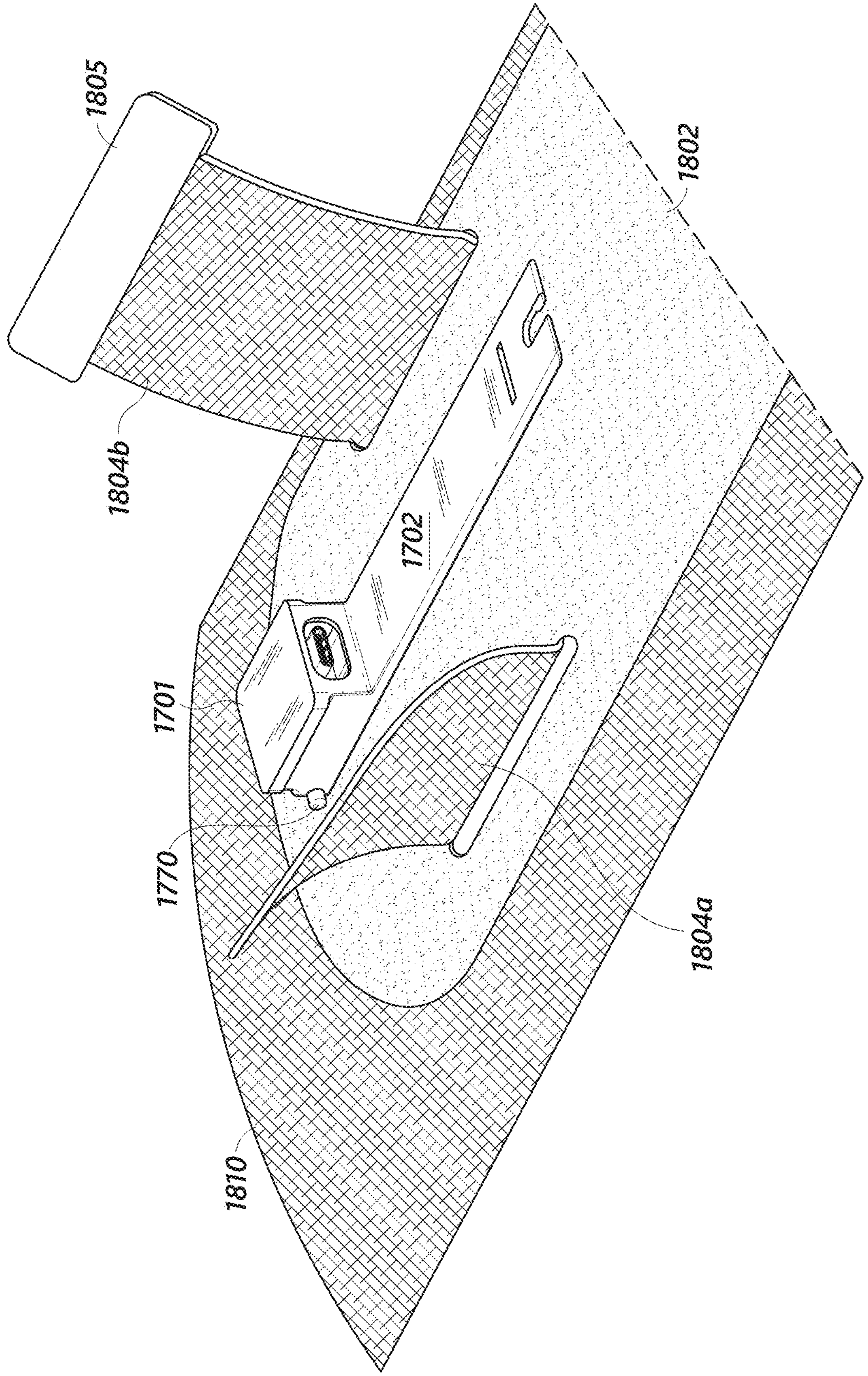

As shown in FIGS. 11A-C and discussed above, outer plate 1702 and inner plate 1722 can connect to each other with the suit 1810 in between. The outer plate 1702 provides a mechanical connection 242 for the control box 152, for example at both securing groove 1734 and cover 1701. An electrical connection 244 is provided at the same connection area 140, 240, for example via electrical connector 1716. An additional mechanical connection 242 can optionally be provided via securing straps 1804*a* and 1804*b*. Mating straps 1804*a* and 1804*b* can be tightened over or around the control box 152 and fastened together, for example via hook-and-loop attachment 1805. Other additional mechanical connections 242 are also suitable, for example a hook-and-loop strap with optional buckle, an elastic band, and/or a pocket as shown in FIGS. 1-2.

Figure 12A:
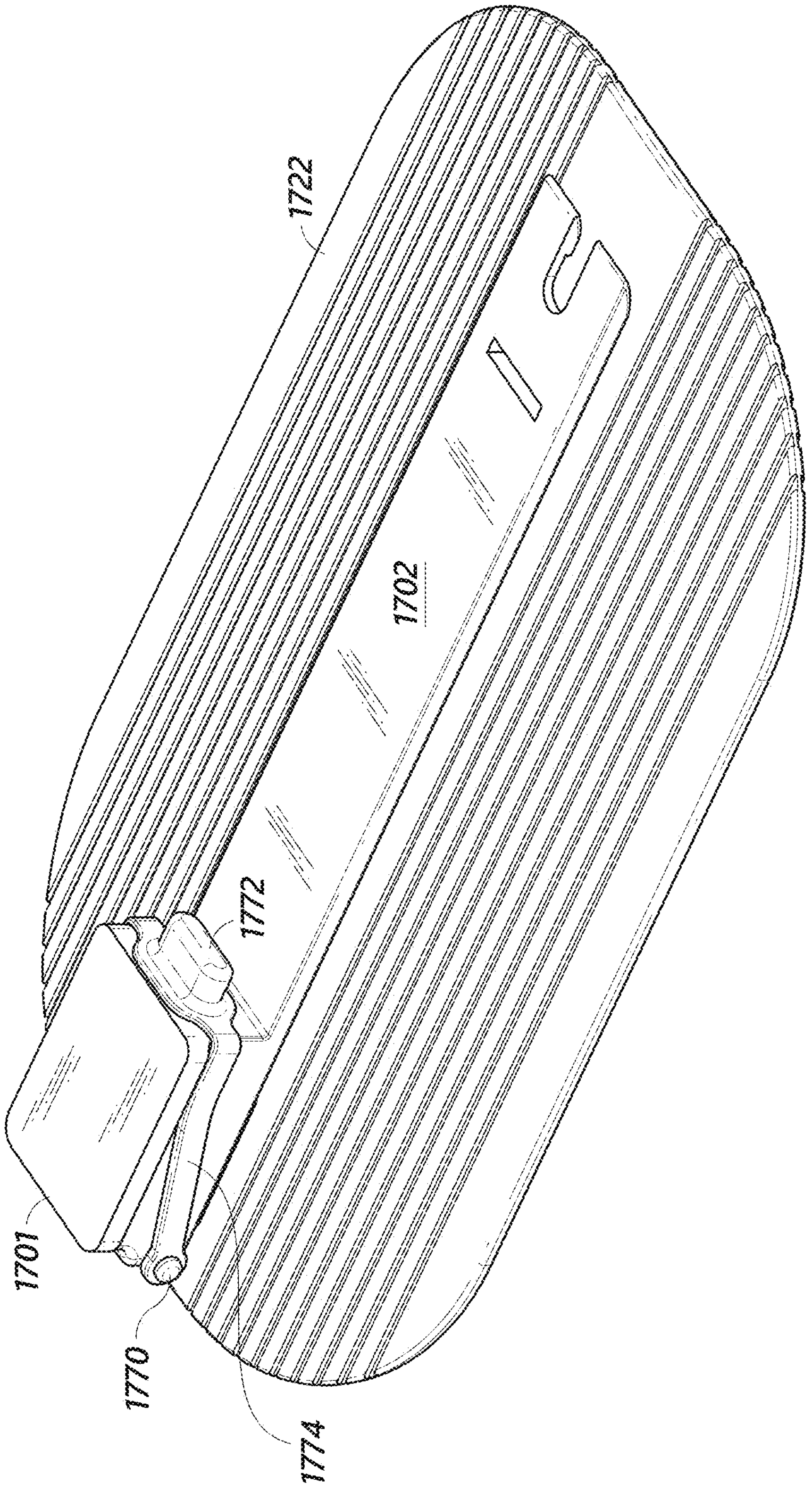
FIGS. 12A and 12B illustrate an implementation of a connection seal of the control box connection.
Figure 12B:
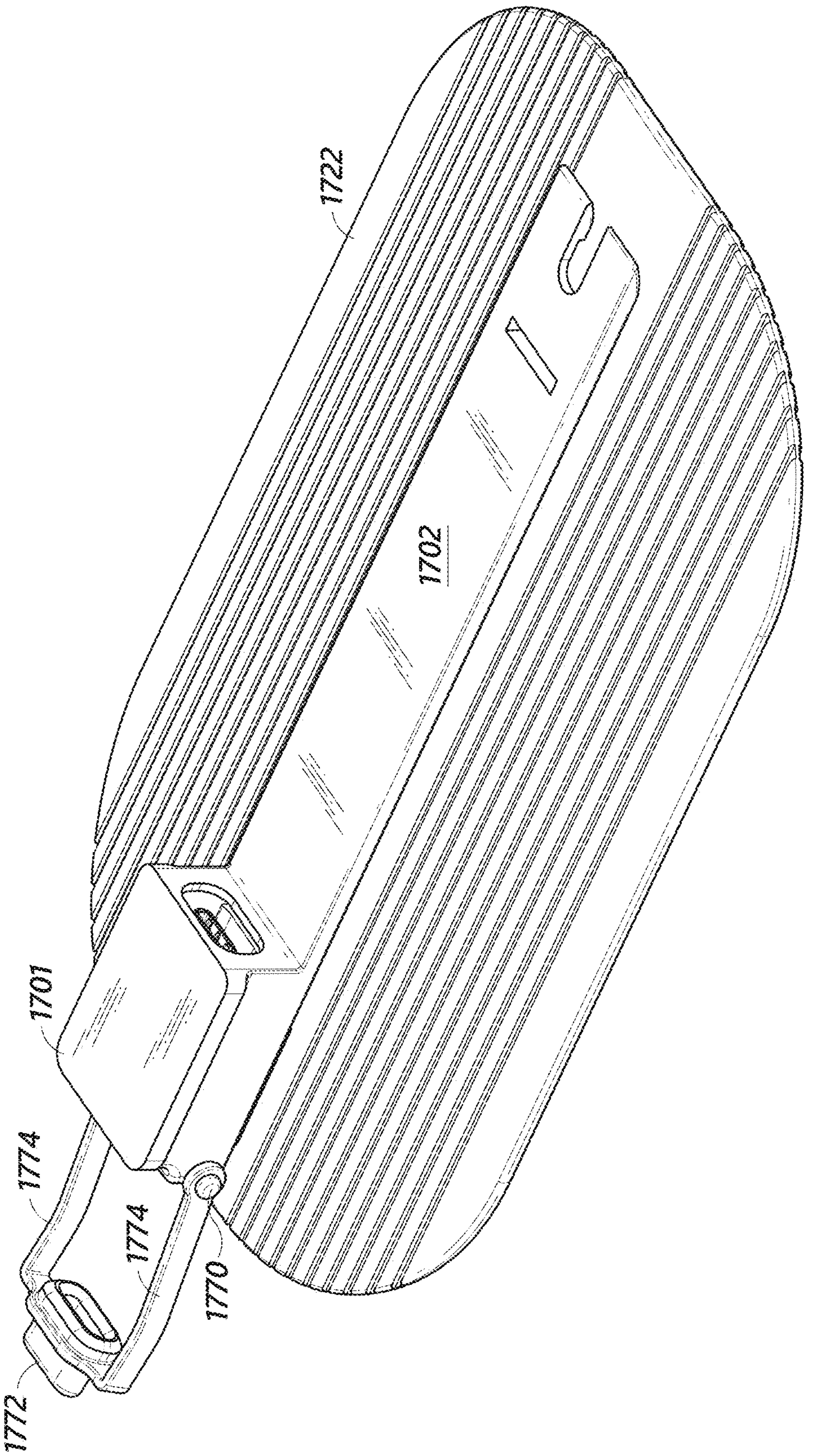

In some implementations, the outer plate 1702 further includes a connection cover 1772. The connection cover 1772 can be secured over the electrical connection 1716, which is similar to connections 1216 and/or 1316 in some or all respects as discussed above. The connection cover 1772 can be secured to the sheet 110, 210. In some implementations, the connection cover 1772 is secured to the outer plate 1702 at pins 1770. As shown in FIG. 12A, when the sheet 110, 210 and/or the connection area 140, 240 is not in use, for example during laundering of the sheet 110, 210, or if the control box 152 is connected to a different connection area 140, 240 on the other side of the sheet 110 or another sheet 110, the cover 1772 fits over the connection 1716 to form a seal. In some implementations, the seal is a dustproof and/or watertight seal. As shown in FIG. 12B, the cover 1772 pivots on pins 1770 to expose the connection 1716. In some implementations, the cover 1772 moves to a flattened position and does not interfere with the connection to the control box 152. The cover 1772 can also include arms 1774, which can function as hinge arms (with pins 1770) and/or tethers in some implementations.

In the examples illustrated in FIGS. 6-12, the electrical connectors 1216, 1316, and 1716 are each a USB-C connector, although other standard connectors are also suitable. For example, the electrical connector 416 could be USB-A, mini-B USB, micro USB, Fire Wire, Lightning, RJ-11, RJ-45 and other suitable connectors.

In some implementations, such as sheets 110 and 210, the connection area 140, 240 is located on one side of the sheet 110. In some implementations, the sheet 110, 210 includes multiple connection areas 140 with associated signal pathways 130, where one connection area 140 is on one side of the sheet 110 and another connection area 140 is on the other side of the sheet 110 (e.g., connection areas 140 and signal pathways 130 on the left and right sides). In these implementations, the control box 152, including at least stimulation controller 150, can be connected to the first or second connection area 140 to allow the stimulation controller 150 to be conveniently located on either side of the surface 20.

As discussed above, the control box 152, including stimulation controller 150, is generally physically connected to the electrodes 120, 220 and any sensors 160 (permanently or via releasable connector). Optionally, these components can be wirelessly connected. Appropriate wireless protocols include infrared (IR), Bluetooth™, WiFi, Zigbee, and RFID. In some wireless implementations, transmission can occur in frequency bands such as the Industrial, Scientific, Medical (ISM) bands, which include 900 MHZ, 2.4 GHZ, 5.2 GHZ, and 5.8 GHz. In some implementations, all the components are connected wirelessly. In some implementations, a portion of the components are connected wirelessly. In some implementations, some or all of the components use both wireless and wired connections. In implementations where wireless communications are used, the connected components, for example wireless sensors 160, further include a transmitter, receiver, or transceiver and an appropriate power source. In some implementations with wireless electrodes, the electrodes 120, 220 may include an integrated power source and signal amplification or an integrated signal generator. In some implementations with wireless sensors, the sensors 160 may have integrated amplification, A/D converters, and/or memory cells for calibration, allowing for some signal conditioning directly on the sensor before transmission.

Control Box

In many implementations, the stimulation controller 150 is housed in a control box 152 that is attached to the sheet 110, 210, 270 at a connection area 140, 240. The stimulation controller 150 provides electrical stimulation signals to the electrodes 120, 220 over the signal pathway 130, 230. In some implementations, the stimulation signal includes the frequency, pulse width, wave form (shape, length, and amplitude), duration, time period (rest) between signals, and/or duty cycle to each electrode 120, 220 sent via the signal pathway 130, 230 and electrical connection 244. In several implementations, the signal is sent every 12-350 milliseconds, but transmissions are not limited to that time span. In accordance with several implementations, the stimulation controller 150 can be detachably connected to the signal pathway 130, 230 sheet 110, 210, and can be moved from signal pathway 130 to another signal pathway 130 on the same sheet 110 or a different sheet 110, as discussed above. The electrical stimulation signals provided to the electrodes 120, 220 advantageously cause a contraction of the target musculature and/or nerve stimulation.

In some implementations, the stimulation controller 150 is housed in a tablet/pad, laptop, desktop computer, cell phone, smartphone, or other portable computing device and connected, for example, to the electrical connection 244 at the connection area 240 and signal pathway 230 of the sheet 210. In many implementations, the stimulation controller 150 is housed in a control box, such as box 152 in FIG. 1 or box 1900 in FIGS. 14A-E. In many implementations, the control box 152 includes a transceiver to communicate with additional software (e.g., communications interface module or unit) on a programming and/or manager device. In many implementations, the transceiver is a wireless transceiver. Appropriate wireless protocols include infrared (IR), Bluetooth™, WiFi, Zigbee, and RFID. In some wireless implementations, transmission between the control box 152 and the other software (e.g., communication interface of the computing or processing device implementing or executing software stored in memory or non-transitory computer-readable storage medium) can occur in frequency bands such as the Industrial, Scientific, Medical (ISM) bands, which include 900 MHZ, 2.4 GHZ, 5.2 GHz, and 5.8 GHz.

In some implementations, the control box 152 optionally includes user interface elements, such as buttons, switches, lights, speakers, displays, and other input and feedback devices. Some interface elements may be inside the control box 152, while others are on the external surface. In some implementations, the control box 152 includes a power switch and power indicator LED. In some implementations, the control box 152 optionally includes a location switch that can be used to indicate if the stimulation controller 150 is connected from the left or right side of the sheet 110 and/or surface 20, if the stimulation controller 150 is connected at a home, a rehabilitation setting, etc., and/or the type of sheet 110 (shape, size, number of electrodes 120, etc.) to which the controller 150 is connected. In some implementations, a switch can be used as an emergency stop.

Figure 13A:
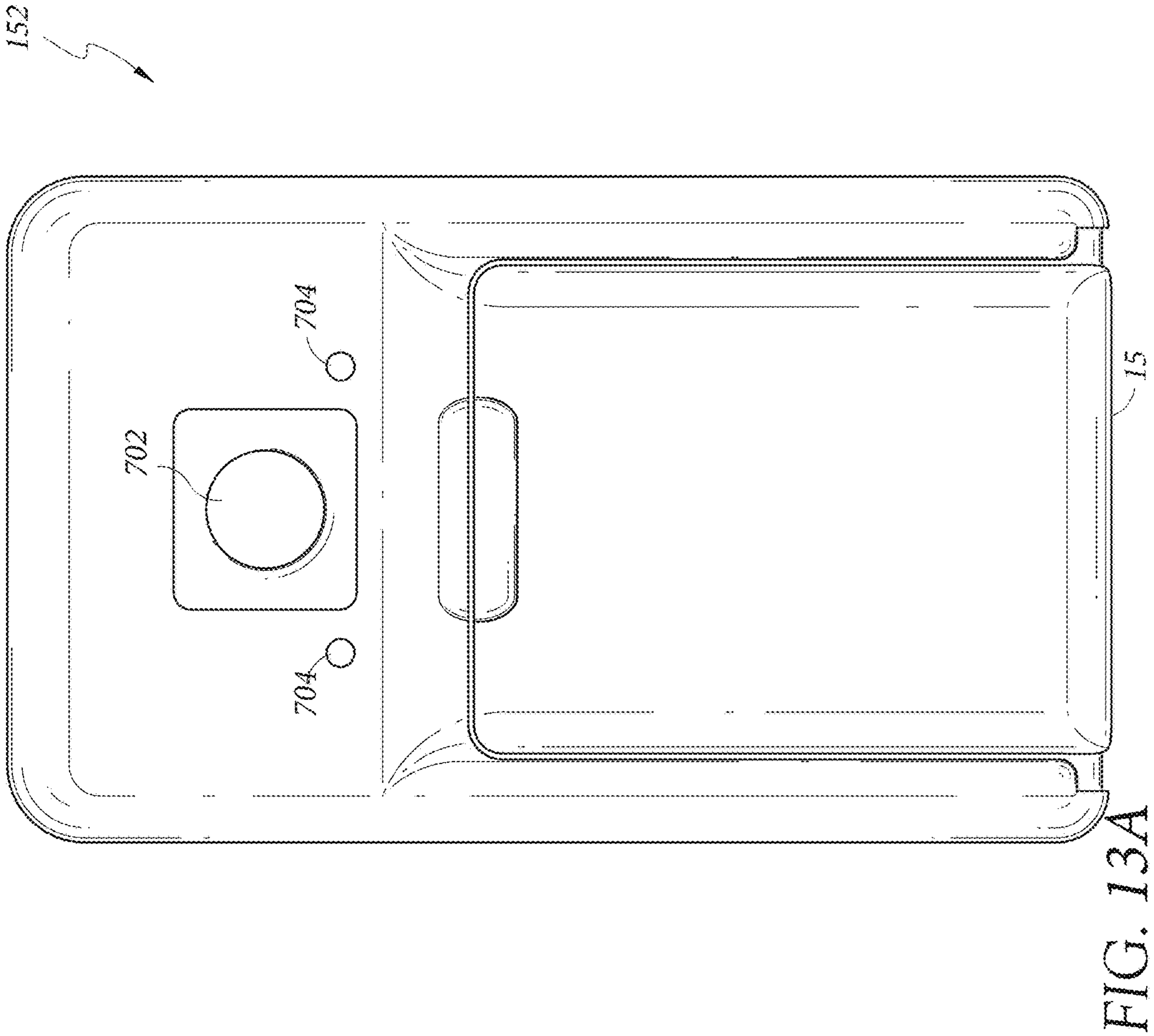
FIGS. 13A and 13B illustrate an implementation of a control box of the system.
Figure 13B:
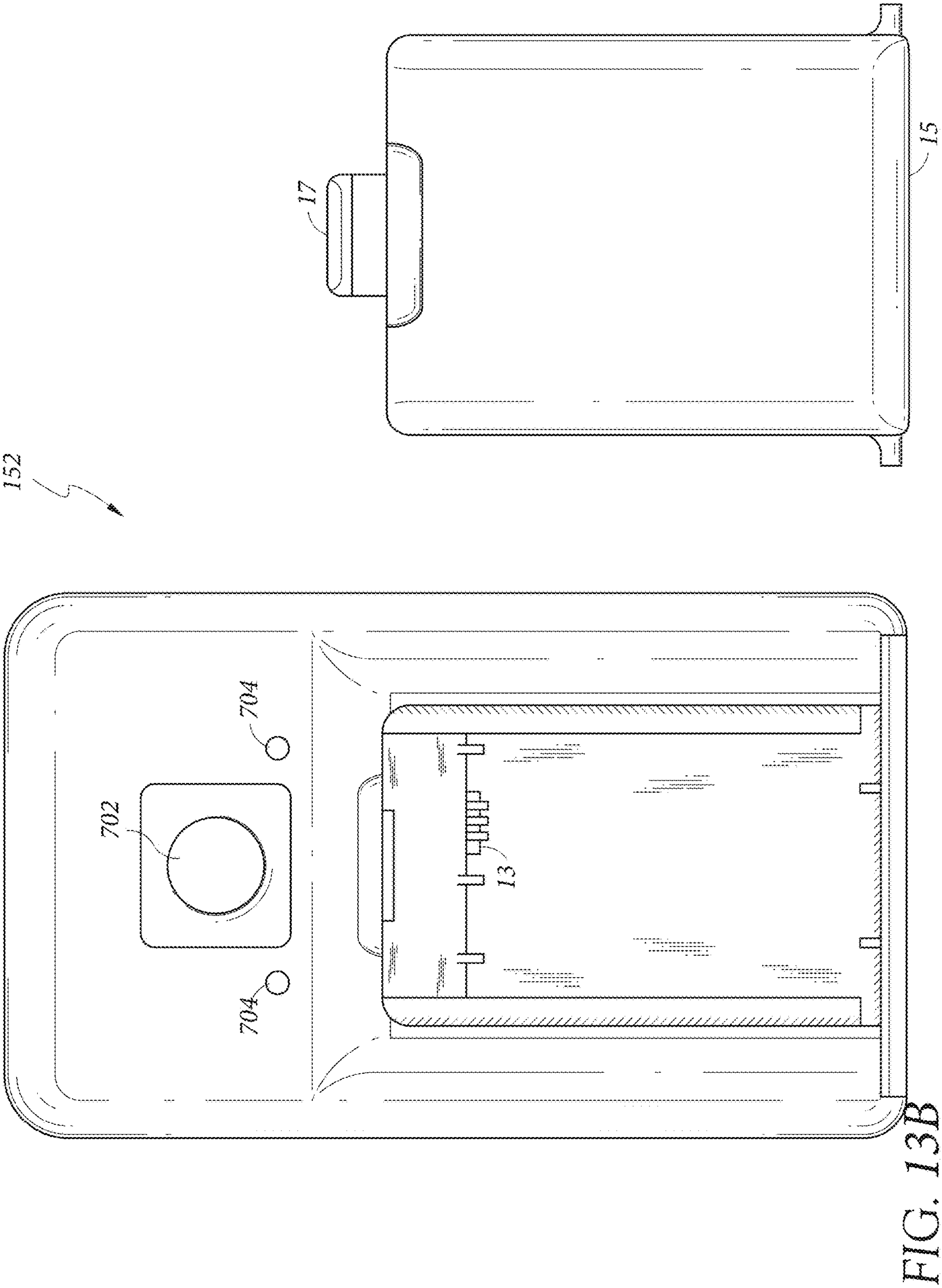

For example, as illustrated in FIGS. 13A-B, control box 152 can include user interface elements, such as a switch and/or indicator light. In some implementations, the switch is a power switch 702. In some implementations, multiple switches are included for power on/off, stimulation start/stop, event marking, assistance request, and the like. In some implementations, the switch is a pushbutton switch, although other switches, such as momentary, rocker, blade, and slide switches are appropriate. In some implementations, indicator lights 704 are LED lights. In some implementations, indicator lights 704 are LED lights that indicate power on/off states, battery charge status, connectivity status, and/or error conditions. In the implementation illustrated in FIGS. 19A-E, control box 1900 includes button 1902 and lights 1904 that may be similar to switch 702 and lights 704 in some or all respects. In some implementations, the control box 152, 1900 can include an integrated switch 702 and light 704, for example an illuminated or backlit switch.

Figure 15:
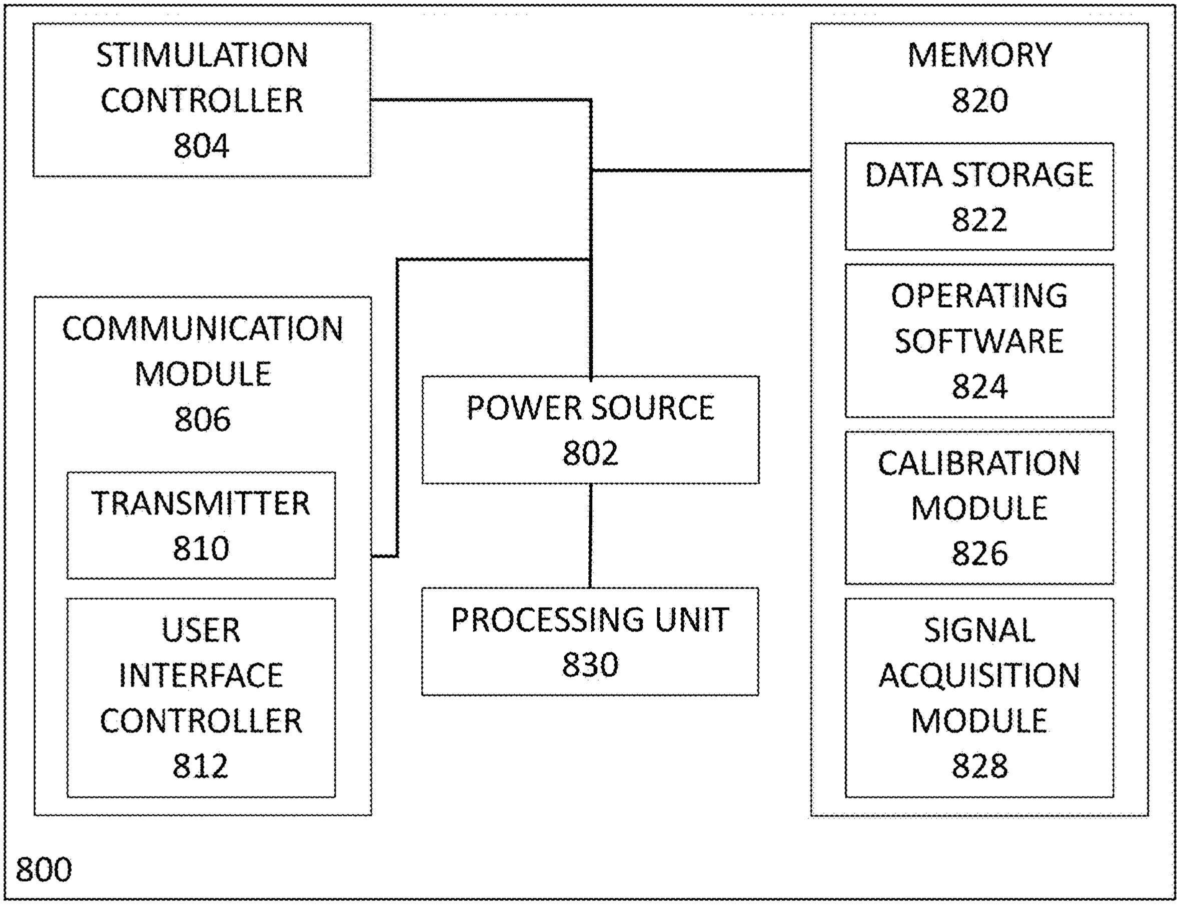
FIG. 15 is a schematic of an implementation of a control box.

FIG. 15 illustrates an example implementation of a control box 800, which may be similar or identical to control box 152 in some or all respects. As shown in FIG. 15, The control box 800 may include a power source 802 connected to the stimulation controller 804. In some implementations, the power source 804 is also connected to a communication module 806 and a memory 820. In some implementations, the power source is a power regulator or conditioner that converts AC line power to a stable DC supply. In this case, the control box 152, 800 may also include a suitable plug, adaptor, or other connection to receive AC power. In some implementations, the power source is a DC power supply such as a battery. In some implementations, the battery includes a main battery and a backup battery. In some implementations, the battery is rechargeable. In this case, the control box may also include a charging circuit and/or the system 100 may include a charging cable or station. In some implementations, the battery is located in a battery housing and is optionally removable or accessible via an openable cover of the controller box.

With reference to FIGS. 13A-B and 14A-E, control box 152, 1900 includes a power source. In some implementations, the power source is a battery. In some implementations, the power source is a removable battery, such as a removable and rechargeable battery. In some implementations, the battery is a 7.4 V DC rechargeable lithium battery 13. In some implementations, the battery is a set of AA, AAA, C, or other size alkaline or nickel-cadmium batteries. In some implementations, the battery 13 is contained in a compartment with a cover 15. In some implementations, the cover 15 is a removable cover with a retention clip 17. In some implementations, such as the example shown in FIGS. 14A-E, battery 1908 in control box 1900 is secured with a sliding battery cover 1906.

In many implementations, the control box 152 includes a connection port for connecting the signal pathway, for example signal pathway 130 and/or signal pathway 230, to the stimulation controller 150 and optionally to other elements inside the control box 152 (e.g., a signal acquisition unit). In some implementations, such as those discussed above, the signal pathway 130, 230 is integrated into the sheet 110, 210, and the electrical connection 244 includes a male/female connection port sewn into or otherwise attached to the sheet 110, 210. The mating male/female connection port is provided on the control box 152. As noted above, in some implementations, the connection port provides both an electrical connection 244 for the stimulation controller 150 and a mechanical connection 242 for the control box 152. In some implementations, the connection area 140, 240 includes a magnetic connection plate, such as connection plate 9 illustrated in FIG. 5. The connection plate 9 can include both metallic leads 17 for the electrical connection 244 and magnet connectors 16 for the mechanical connection 242. In this case, the control box 152 includes appropriate mating metallic and/or magnetic or ferromagnetic connections.

Figure 14A:
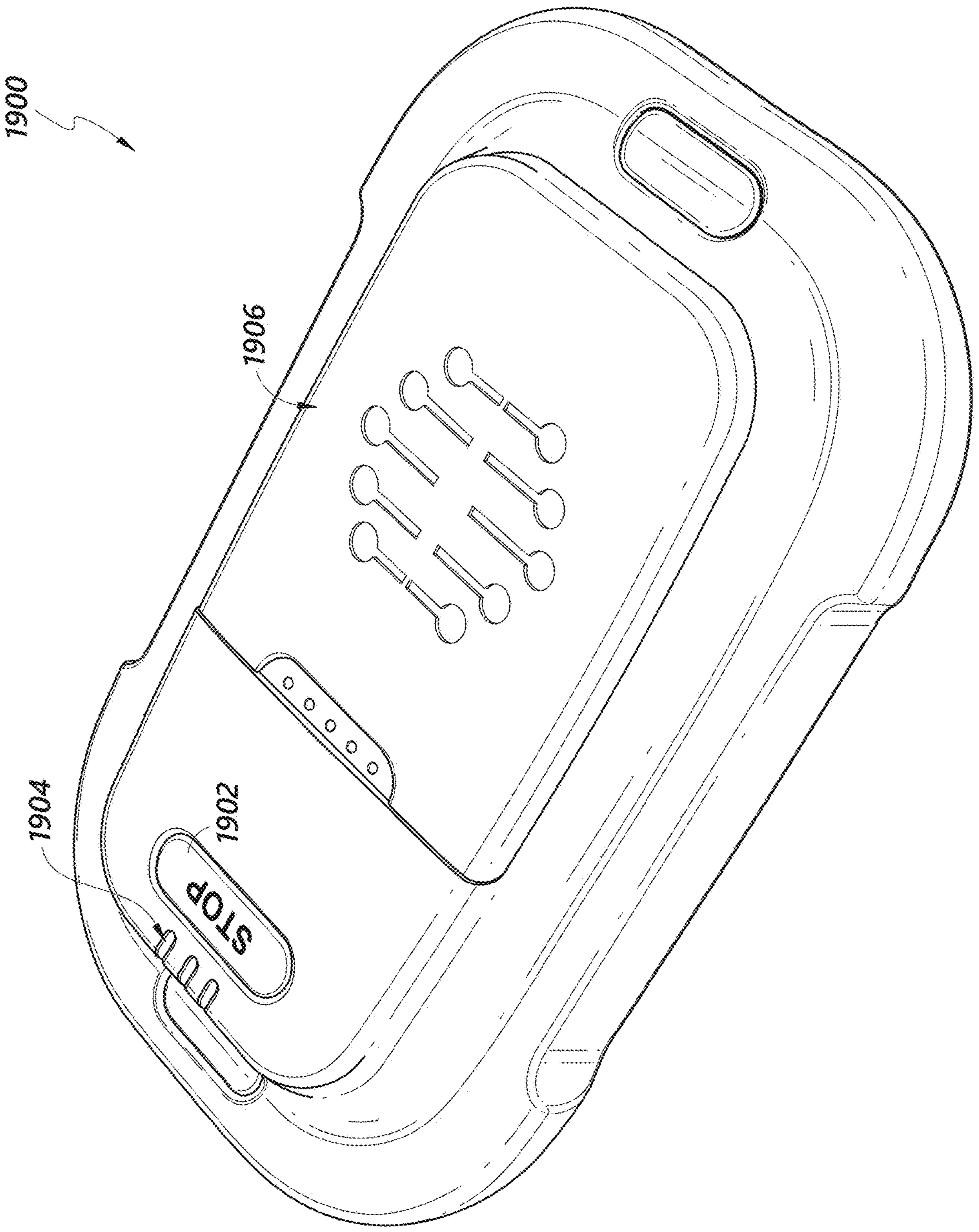
FIGS. 14A, 14B, 14C, 14D, and 14E illustrate an implementation of a control box.
Figure 14B:
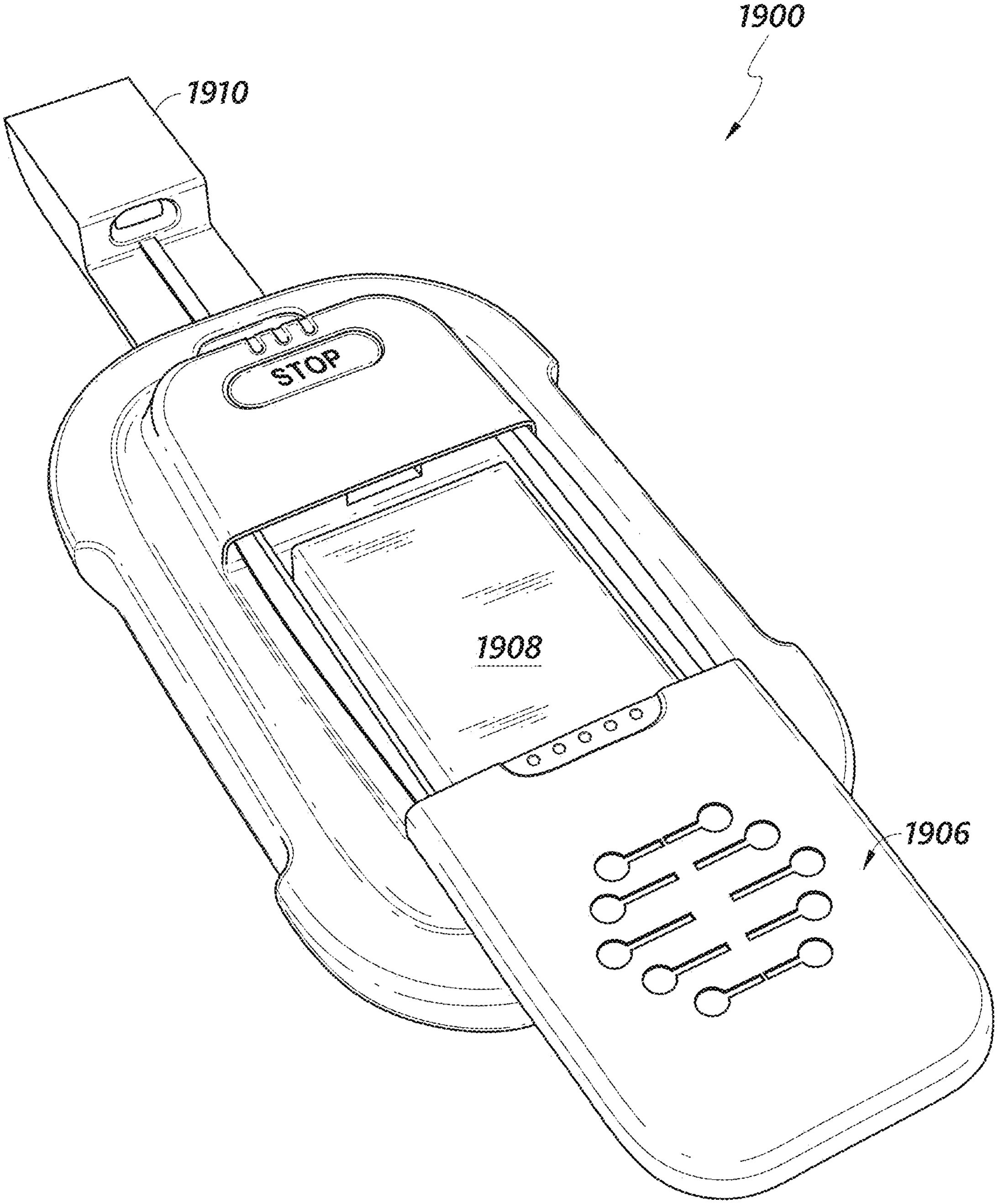
Figure 14C:
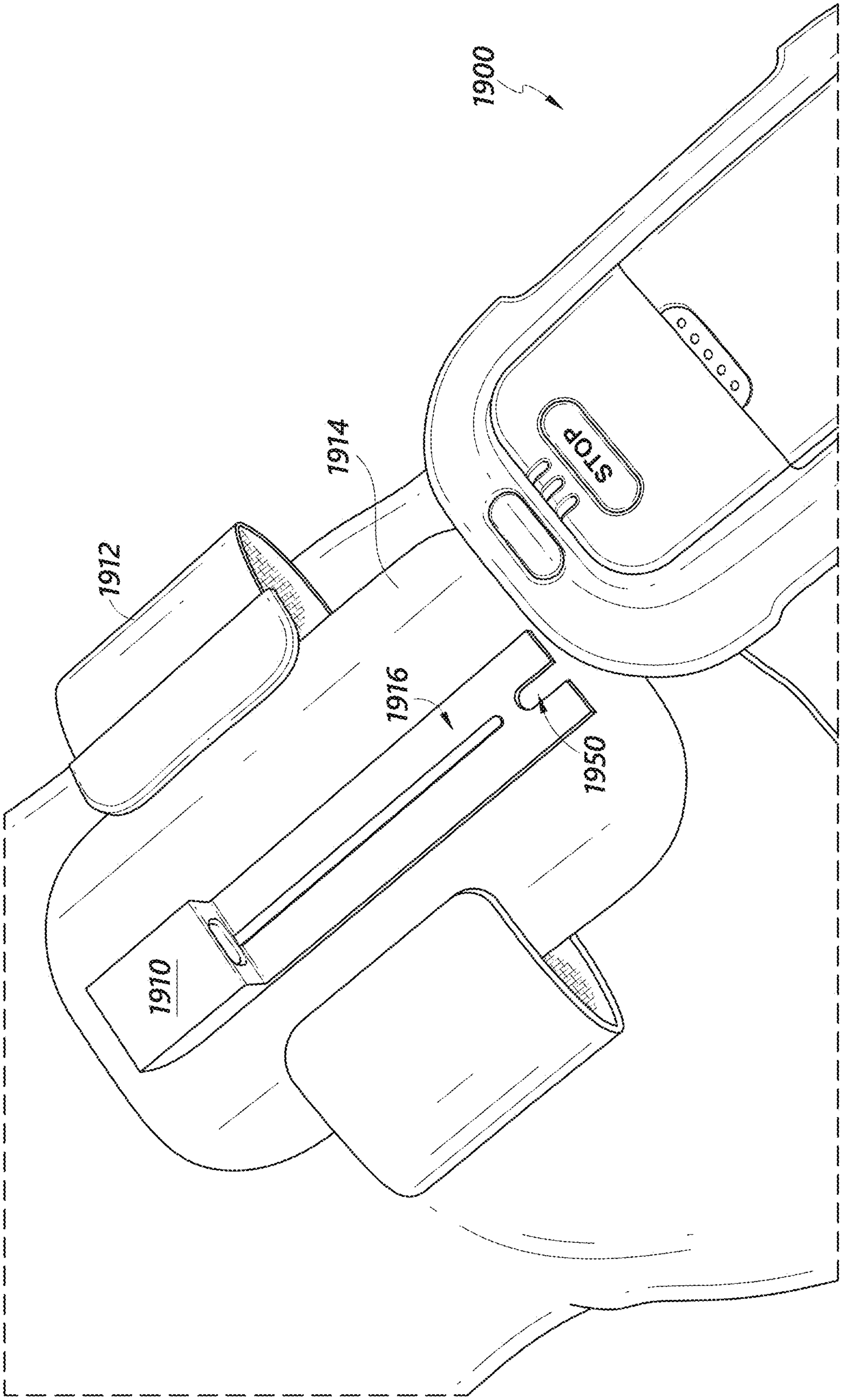
Figure 14D:
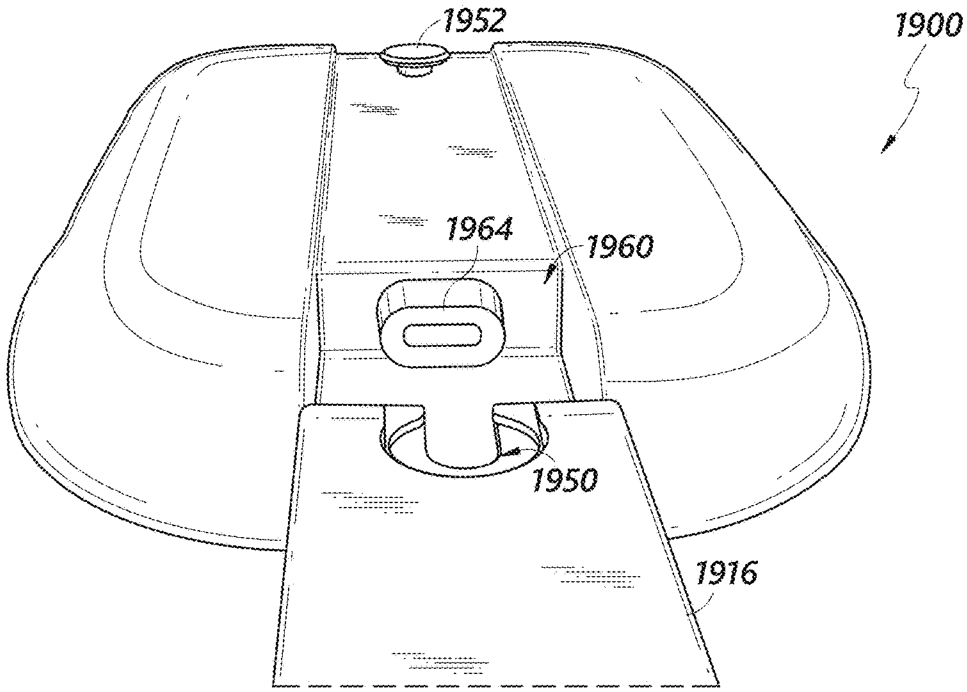
Figure 14E:
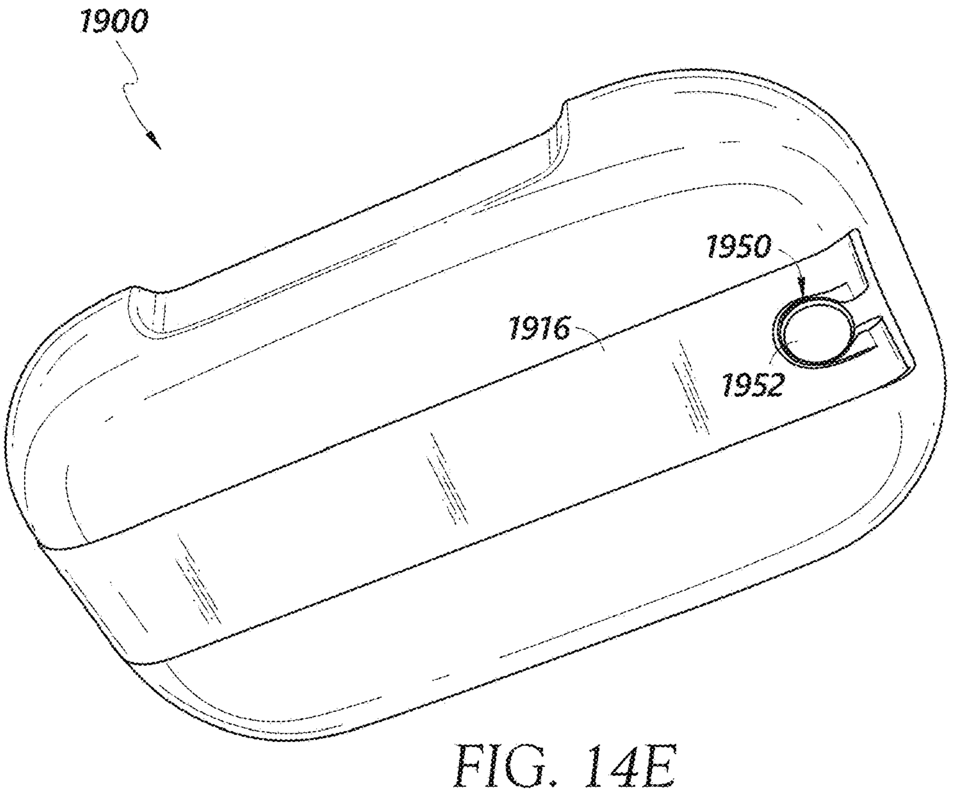

As shown in FIGS. 14C-14E and discussed above with respect to FIGS. 6-12, the control box 1900 is releasably attached to the sheet 110 at a connection area 140. In this example, the connection area 140 includes an upper plate 1916 with a housing 1910 containing the electrical connector, securing straps 1912, and a reinforcement or support plate 1914. These features can be similar to the corresponding plates, straps, and connectors discussed above in some or all respects. In some implementations, upper plate 1916 includes an alignment rail used to slide in a mating slot or groove on the back of control box 1900. In this implementation, the upper plate 1916 includes at least one securing shape, such as shaped cover 1910 and securing notch 1950. As illustrated in FIGS. 14C-E, the back of control box 1900 includes mating securing shapes, such as post 1952 and recess 1960. When the control box 1900 is connected to sheet 110 at the connection area 140, the upper plate 1916 mates with the back of the control box 1900. In some implementations, securing notch 1950 mates with post 1952 and shaped cover 1910 mates with at least part of recess 1960. These features cooperate to provide at least part of the mechanical connection 242. Additional mechanical connection 242 can be provided by securing straps 1912 over the control box 1900 after it is connected at the connection area 140. The electrical connector inside the shaped cover 1910 (for example, electrical connectors 1216, 1316, 1716) mates with connection port 1964 on the back of the control box 1900. In some implementations, connection port 1964 is located at least partially inside recess 1960 to allow connection port 1964 to connect with the electrical connector 1216, 1316, 1716 to make electrical connection 9 when cover 1910 mates with recess 1960. In some implementations, recess 1960 includes a deep recess for the connection port 1964 that is shaped for the cover 1910, and a shallow recess for upper plate 1916. As illustrated in FIGS. 14D-E, the different areas of the recess 1960 allow the upper plate 1916 to mate with the back of the control box 1900 and provide a flush or smooth surface against the body the patient 10.

These connectors are illustrative, and not intended to limit the system 100, 200 to those methods of connection. As noted above, additional suitable connectors include a hook-and-loop strap, a tie down, or a pocket to securely fasten the control box 1900 to the signal pathway 130 and/or sheet 110. Other connection implementations include a snap, zipper, button, or variations thereof. The control box 1900 may include mating connections (e.g., snaps, zipper halves, buttonholes, etc.) and/or cooperating hooks, clips, loops, tabs, and the like to secure the control box 1900 to the sheet 110 at the connection area 140. These mating features can be provided in addition to or in place of mating features securing notch 1950 and post 1952 and/or mating features recess 1960 and cover 1910. As noted above, in some implementations, the electrical and mechanical connections are separate. In some implementations, the electrical and mechanical connections are integrated or cooperating, such as a conductive metal snap or the conductive magnetic plate connection mentioned above. In some implementations, the electrical connection 244, mechanical connection 242, or both, are permanent. In some implementations, the connections are releasable to allow repeated connecting and disconnecting.

In several implementations, the system is modular, and the control box 152, 1900 can be disconnected and moved. In some implementations, such as those discussed above with respect to the signal pathway 130, 230, the control box 152, 1900 can be moved from a connection area 140 on one side of the sheet 110 to a connection area 140 on the other side of the sheet 110 (for example, from the right side to the left side, or from the top/head side to a bottom/feet side). In some implementations, the control box 152 can be moved from a first sheet (for example suit 110 and the associated signal pathway 130) to another sheet 110. In this way, the first sheet 110 can be replaced with an identical (e.g., clean or new) sheet 110, or replaced with a different sheet 110 having different electrodes 120, electrode locations, and/or a different sheet 110 having a different size, shape, number of electrodes 120, and/or location of electrodes, such as sheet 210. For example, a patient 10 can use the control box 152 with multiple identical sheets 110 used on different days. As another illustrative and non-limiting example, a patient 10 can use a control box 152 with a first sheet 110 that is a bed sheet during sleeping, and then move the control box 152 to a second sheet 110 that is a wheelchair cushion cover.

In some implementations, the control box 152 is portable and capable of being transported relatively easily. In some implementations, the control box 152 is easily moved to the sheet 110 and then carried by the sheet 110 without interfering with other sheet functions (e.g., without pulling a mattress-type sheet 110 off a bed surface 20, or without disrupting balance, rolling, or braking of a wheelchair when connected to a seat cushion-type sheet 110 on a seating surface 20).

The control box 152, including at least stimulation controller 150, and sheet 110, including at least electrodes 120, are operated via operating software and/or firmware. In some implementations, the software and/or firmware is stored in the control box 152 and is programmed to perform a pre-set stimulation pattern via the stimulation controller 150 and electrodes 120. In some implementations, the software is written to operate the stimulation controller 150 and the sheet 110 with electrodes 120 and optional sensors 160, and to communicate with a programming and/or monitoring device, such as a tablet/pad, laptop, desktop computer, cell phone, or other portable computing device.

As illustrated in FIG. 15, the control box 800 includes at least the stimulation controller 804. As discussed above, the control box 800 can also optionally house other system features such as a power source 802, communication module 806, and memory 820. Communication module 806 can allow communication to other devices via transmitter 810 and to a user via user interface controller 812. In some implementations, transmitter 810 is a transceiver. Transmitter 810 can be selected to provide wired and/or wireless communications. User interface controller 812 can provide communication to a user and/or accept input from a user. For example, user interface controller 812 can control indicator lights 704 and accept input from switches 702. In some implementations, user interface controller 812 can provide other input/output functions such as controlling a printer, display, buzzer, speaker, touchscreen, microphone, mouse, stylus, and other interface devices described herein.

Control box 800 can also include a memory 820, which can be connected to power source 802 and stimulation controller 804, and further optionally connected to communication module 806. Memory 820 can include data storage 822, operating software 824, calibration module 826, and signal acquisition module 828. In some implementations, data storage 822 can be used to store data from sensors 160, collected via signal acquisition module 828, calibration data used in calibration module 828, user preferences, location information, and other useful information. In some implementations, data storage 822 is a removable storage module, such as a flash drive, SD card, microSD card, and the like.

In some implementations, the calibration module 826 is used to establish a baseline, a threshold, an offset, a calibration coefficient such as a scaling factor, other calibration parameters, and combinations thereof. A calibration algorithm can be performed for a user 10, a sheet 110, and/or a location. For example, a stimulation threshold can be established for a particular user 10 with a particular sheet 110. When the sheet 110 and/or electrode(s) 120 are replaced for laundering, the new sheet 110 and/or electrode(s) 120 can be recalibrated to ensure safety and function of the new sheet 110 and electrodes 120. Similarly, calibration can be performed when the control box 152 is moved from one signal pathway 130 to another signal pathway 130 (e.g., when the stimulation controller 150 is moved from one side of the bed/sheet 110 to the other side) to account for the different relationships and geometry between the connected components. In some implementations, calibration optionally can be performed when adding, replacing, or removing sensors 160 in order to establish a baseline. In some implementations, calibration information is stored in a memory of the control box 152. In some implementations, stored calibration information can be selected, altered, or accessed via the user interface (e.g., switches 702 and lights 704), for example to choose a specific use case, or to select a generic use case that can be used directly or adjusted into a specific use case. In these implementations, the calibration data can be stored and used as part of a user pre-set pattern. In some implementations, calibration is performed automatically, such as when the system 100 detects a new component connection, on power-up, and/or after a predefined run time. In some implementations, the predefined run time is an hour, twelve hours, twenty-four hours, 3 days, 7 days, 30 days, or 90 days. These examples are illustrative and not intended to be limiting. In some implementations, the calibration can optionally be performed at any time via user selection.

As discussed above, some implementations include sensors 160. In these systems, the control box 152, 800 may further include signal acquisition, processing, and/or transmission components, such as signal acquisition module 828. In some implementations, sensor signals can be used to trigger application of stimulation or an alert to a clinician or other caregiver. For example, temperature and pressure sensors 160 can be used to start stimulation if, for instance, the detected temperature or pressure indicates that pressure ulcers are likely to form. For example, sensors 160 may sense pressure and/or lack of circulation in an area that triggers stimulation based on the sensing and continuously adjusts the stimulation based on the sensing over time. The measured parameters may be used to trigger a correct amount of stimulation to be provided (e.g., intensity, duration, or other stimulation characteristics). In some implementations, wetness sensors can stop stimulation and/or indicate the system 100 needs to be cleaned/changed. Data from a pH sensor can indicate skin health and can suggest treatment changes. Data from an impedance sensor can indicate skin breakdown or the presence of a wound, and can be used to stop stimulation. An impedance sensor can also indicate a "leads off" condition and automatically stop stimulation and trigger an alert (a light such as light 754, a buzzer, a notification at a nursing station, and the like). In some implementations, the collected data from sensor(s) 160 are used to adjust the provided stimulation, including starting and stopping stimulation, via stimulation controller 150, 804. In some implementations, the collected data from sensor(s) 160 are transmitted to a health care provider or electronic medical record. These sensors 160 and sensor uses are illustrative only, and are not limiting or required.

In some implementations, the system comprises various features that are present as single features (as opposed to multiple features). For example, in one implementation, the system includes a single sheet, a single electrode, and a single control box with a stimulation controller. The sheet may form a single, unitary, or integral, construct including the textile sheet, electrode(s), signal pathway(s), and connection area. In some implementations, multiple sensors may be contained in an integrated sensor package. For example, multiple photodetectors can be combined with a thermistor in an integrated sensor package. In some implementations, the control box includes a single integrated package including a stimulation controller, transceiver, charging circuit, and memory. In some implementations, the software is a single software package, while in other implementations the software is made of multiple cooperating modules optionally run on distributed hardware. Multiple features or components are provided in alternate implementations.

In some implementations, the system comprises one or more of the following: a means for muscle stimulation (e.g., electrodes, wires), a means for holding the stimulation means against the muscle or skin (e.g., a sheet, garment, belt, strap, band, harness, adhesive), a means for controlling the stimulation (e.g., a software based controller, a hardware based controller, a pre-programmed controller, a dynamically adjustable controller), a means for interfacing with a user (e.g., a button, switch, light, speaker, display, touchscreen, mouse, stylus), a means for biosensing (e.g., electrodes, sensors, signal acquisitioning circuitry, signal processors and pre-processors), and a means for data analysis and storage (artificial intelligence, data sets, memory, removable memory, servers).

In general, the word "module," as used herein, refers to logic embodied in hardware or firmware or to a collection of software instructions, having entry and exit points. Modules are written in a program language, such as JAVA, C or C++, PYPHON or the like. Software modules may be compiled or linked into an executable program, installed in a dynamic link library, or may be written in an interpreted language such as BASIC, PERL, LUA, or Python. Software modules may be called from other modules or from themselves, and/or may be invoked in response to detected events or interruptions. Modules implemented in hardware include connected logic units such as gates and flip-flops, and/or may include programmable units, such as programmable gate arrays or processors.

Generally, the modules described herein refer to logical modules that may be combined with other modules or divided into sub-modules despite their physical organization or storage. The modules are executed by one or more computing systems and may be stored on or within any suitable computer readable medium or implemented in-whole or in-part within special designed hardware or firmware. Not all calculations, analysis, and/or optimization require the use of computer systems, though any of the above-described methods, calculations, processes, or analyses may be facilitated through the use of computers. Further, in some implementations, process blocks described herein may be altered, rearranged, combined, and/or omitted.

In some implementations, the control box 152, 800 includes one or more processing units (CPU) 830, which may comprise a microprocessor. As noted above, the control box 152, 800 can include a physical memory, such as memory 820, which may be, for example, random access memory (RAM) for temporary storage of information, a read only memory (ROM) for permanent storage of information, and/or a mass storage device such as a backing store, hard drive, rotating magnetic disks, solid state disks (SSD), flash memory, phase-change memory (PCM), 3D XPoint memory, diskette, or optical media storage device. Alternatively, the mass storage device may be implemented in an array of servers. Such servers or other remote data storage systems can be accessed via transmitter 810, and/or a dedicated data transceiver. Typically, the components of the control box 152, 800 are connected using a standards-based bus system. The bus system can be implemented using various protocols, such as Peripheral Component Interconnect (PCI), Micro Channel, SCSI, Industrial Standard Architecture (ISA) and Extended ISA (EISA) architectures, as well as other protocols suitable for providing power and data transfer.

As illustrated in FIG. 15, the control box 152, 800 can include a user interface controller 812 to operate one or more input/output (I/O) devices and interfaces, such as a keyboard, mouse, touch pad, and printer. The I/O devices and interfaces can include one or more display devices, such as a monitor, that allows the visual presentation of data to a user. More particularly, a display device provides for the presentation of GUIs as application software data, and multi-media presentations, for example. The I/O devices and interfaces can also provide a communications interface to the user and/or various external devices. The control box 152, 800 may comprise a user interface controller 812 for one or more multi-media devices, such as speakers, video cards, graphics accelerators, and microphones, for example. These devices can be provided in and/or on the control box 152, 800, or can be removably connected to the control box 152, 800, via appropriate adaptors, ports, cables, harnesses, plugs, and the like.

The user interface controller 812 may be implemented to control a combination of an all-points addressable display such as a cathode ray tube (CRT), a liquid crystal display (LCD), a plasma display, or other types and/or combinations of displays. The user interface controller 812 may be implemented to communicate with input devices and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition, a touch screen may act as a hybrid input/output device.

In some implementations, some or all of the above functions are incorporated into the control box 152, 800, which operates as a standalone device to deliver electrical stimulation to the electrodes 120 and optionally collect data from sensors 160.

Stimulation Patterns

As indicated above, the system 100 delivers electrical stimulation to the electrodes 120 on sheet 110, and thereby to the patient 10. Stimulation is generated by a series of repeated pulses. In some implementations, the pulses are generally uniform, and can be delivered at a varying frequency. For example, in some implementations, each uniform pulse is a symmetric square wave, made of two equal phases with 0 microseconds between phases. The equal phases can be 20-400 microseconds each. Because the pulse is biphasic and symmetrical, electricity flows in both directions and is balanced. In accordance with several implementations, as there is no net ion flow, this stimulation activates nerves and muscles but does not create a residual build-up of ions.

These uniform pulses are grouped into pulse trains. A pulse train is a set of pulses delivered at a frequency for a period of time (the "on" time) followed by a delay (or an "off" time). For many implementations, the frequency and/or timing (the on/off times, or a duty cycle) is adjustable. The stimulation output may have an amplitude between 0 and 200 mA. The stimulation output may be constant current type and have a frequency range of between 1 and 120 Hz (e.g., between 1 and 100 Hz, between 5 and 75 Hz, between 20 and 60 Hz, and other sub-ranges within 1-120 Hz, and/or any frequency within the range). The stimulation output pulse width may vary between 75 and 400 microseconds (e.g., between 80 and 350 microseconds, between 100 and 300 microseconds, between 200 and 250 microseconds, between 75 and 180 microseconds, and other sub-ranges within 75-500 microseconds, as well as any pulse width within the range). In some implementations, the output voltage range is between 7 and 80 volts (e.g., between 10 and 75 volts, between 20 and 60 volts, between 30 and 50 volts, between 12 and 25 volts, and other sub-ranges within 7-80 volts, as well as any voltage within the range). In some implementations, the stimulation output pulse ramp up and down may range from 0 to 2 seconds (e.g., 0 to 1.0 seconds, 0.25 seconds to 0.75 seconds, and other sub-ranges within 0-2 seconds, as well as any ramp time within the range), as desired and/or required. The ramp up may be toggled between three discrete levels of abrupt, medium and gentle ramp up and ramp down.

Stimulation parameters (e.g., amplitude, frequency, duration of activation and relaxation phases) may be designed (e.g., pre-programmed) to target particular muscles and/or anatomic locations (e.g., target areas 12) to tailor the stimulation program to enhance or maximize the effects. In some implementations, stimulation is provided to all target areas 12 (e.g., all electrodes 120) together, while in some implementations, stimulation is provided to targets 12 with sequential or overlapping timing.

In one example stimulation mode, stimulation can be provided for a massage function. In this implementation, a muscle or group of muscles can be burst-activated activated for a maximal or near-maximal contraction for a short time period, followed by a longer rest period. For example, a muscle or group of muscles can be activated using a pattern of stimulation at 84 Hz for 1 second, followed by 4 seconds of rest, which is repeated. As another example, a muscle or group of muscles can be activated using a stimulation pattern of stimulation at 84 Hz for 180 microseconds, followed by 75 microseconds of rest, which pattern is repeated.

In another example stimulation mode, stimulation is provided to induce muscle and/or nerve stimulation for muscle toning. In this implementation, again a muscle or group of muscles can be activated for a time period, followed by a rest period. The activation/rest durations are similar to strength training, but the frequency of stimulation is different. In some implementations, the frequency is lower to provide sub-maximal muscle contractions. For example, a muscle or group of muscles can be activated using a pattern of stimulation at 40 Hz for 4 seconds, followed by 4 seconds of rest, which is repeated, or stimulation at 40 HZ for 180 microseconds followed by 75 microseconds of rest. In some implementations, the frequency is very high to provide maximal contraction. For example, a muscle or group of muscles can be activated using a repeating cycle of stimulation at 100 Hz for 5 seconds, followed by 3 seconds of rest or, alternatively, 100 Hz stimulation for 75 microseconds, followed by 180 microseconds of rest.

As noted above, stimulation can be provided to all electrodes 120 in concurrent, individual, sequenced, and/or overlapping schemes. In many of the stimulation modes, each cycle is repeated immediately after conclusion of the prior cycle, and the pattern continues for a session duration, for example 1, 2, 3, 5, 10, 12, 15, minutes or other appropriate time. In many of the stimulation modes, the session is repeated after an appropriate delay, for example 0.5, 1, 2, 4, 6, 8, 12, 18, 24 hours or other appropriate interval.

Additional Implementations

In the foregoing specification, the invention has been described with reference to specific implementations thereof. It will, however, be evident that various modifications and changes may be made thereto without departing from the broader spirit and scope of the invention. The specification and drawings are, accordingly, to be regarded in an illustrative rather than restrictive sense.

Indeed, although this invention has been disclosed in the context of certain implementations and examples, it will be understood by those skilled in the art that the invention extends beyond the specifically disclosed implementations to other alternative implementations and/or uses of the invention and obvious modifications and equivalents thereof. In addition, while several variations of the implementations of the invention have been shown and described in detail, other modifications, which are within the scope of this invention, will be readily apparent to those of skill in the art based upon this disclosure. It is also contemplated that various combinations or sub-combinations of the specific features and aspects of the implementations may be made and still fall within the scope of the invention. It should be understood that various features and aspects of the disclosed implementations can be combined with, or substituted for, one another in order to form varying modes of the implementations of the disclosed invention. Any methods disclosed herein need not be performed in the order recited. Thus, it is intended that the scope of the invention herein disclosed should not be limited by the particular implementations described above.

It will be appreciated that the systems and methods of the disclosure each have several innovative aspects, no single one of which is solely responsible or required for the desirable attributes disclosed herein. The various features and processes described above may be used independently of one another or may be combined in various ways. All possible combinations and subcombinations are intended to fall within the scope of this disclosure.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination. No single feature or group of features is necessary or indispensable to each and every implementation.

As used herein, "system," "instrument," "apparatus," and "device" generally encompass both the hardware (for example, mechanical and electronic) and, in some implementations, associated software (for example, specialized computer programs for graphics control) components.

It is to be understood that not necessarily all objects or advantages may be achieved in accordance with any particular implementation described herein. Thus, for example, those skilled in the art will recognize that certain implementations may be configured to operate in a manner that achieves or optimizes one advantage or group of advantages as taught herein without necessarily achieving other objects or advantages as may be taught or suggested herein.

Each of the processes, methods, and algorithms described in the preceding sections may be embodied in, and fully or partially automated by, code modules executed by one or more computer systems or computer processors including computer hardware. The code modules may be stored on any type of non-transitory computer-readable medium or computer storage device, such as hard drives, solid state memory, optical disc, and/or the like. The systems and modules may also be transmitted as generated data signals (for example, as part of a carrier wave or other analog or digital propagated signal) on a variety of computer-readable transmission mediums, including wireless-based and wired/cable-based mediums, and may take a variety of forms (for example, as part of a single or multiplexed analog signal, or as multiple discrete digital packets or frames). The processes and algorithms may be implemented partially or wholly in application-specific circuitry. The results of the disclosed processes and process steps may be stored, persistently or otherwise, in any type of non-transitory computer storage such as, for example, volatile or non-volatile storage.

Many other variations than those described herein will be apparent from this disclosure. For example, depending on the implementation, certain acts, events, or functions of any of the algorithms described herein can be performed in a different sequence, can be added, merged, or left out altogether (for example, not all described acts or events are necessary for the practice of the algorithms). Moreover, in certain implementations, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm elements described in connection with the implementations disclosed herein can be implemented as electronic hardware, computer software, or combinations of both. To clearly illustrate this interchangeability of hardware and software, various illustrative components, blocks, modules, and elements have been described herein generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various features and processes described herein may be used independently of one another, or may be combined in various ways. All possible combinations and sub-combinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example implementations. The example systems and components described herein may be configured differently than described. For example, elements may be added to, removed from, or rearranged compared to the disclosed example implementations.

The various illustrative logical blocks and modules described in connection with the implementations disclosed herein can be implemented or performed by a machine, such as a general purpose processor, a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. In another implementation, a processor includes an FPGA or other programmable devices that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. Although described herein primarily with respect to digital technology, a processor may also include primarily analog components. For example, some, or all, of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, or algorithm described in connection with the implementations disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC. The ASIC can reside in a user terminal. In the alternative, the processor and the storage medium can reside as discrete components in a user terminal.

It will also be appreciated that conditional language used herein, such as, among others, "can," "could," "might," "may," "e.g.," and the like, unless specifically stated otherwise, or otherwise understood within the context as used, is generally intended to convey that certain implementations include, while other implementations do not include, certain features, elements and/or steps. Thus, such conditional language is not generally intended to imply that features, elements and/or steps are in any way required for one or more implementations or that one or more implementations necessarily include logic for deciding, with or without author input or prompting, whether these features, elements and/or steps are included or are to be performed in any particular implementation. The terms "comprising," "including," "having," and the like are synonymous and are used inclusively, in an open-ended fashion, and do not exclude additional elements, features, acts, operations, and so forth. In addition, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise. Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one more example processes in the form of a flowchart. However, other operations that are not depicted may be incorporated in the example methods and processes that are schematically illustrated. For example, one or more additional operations may be performed before, after, simultaneously, or between any of the illustrated operations. Additionally, the operations may be rearranged or reordered in other implementations. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

Further, while the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain implementations require at least one of X, at least one of Y, and at least one of Z to each be present. The section headings provided herein, if any, are for convenience only and do not necessarily affect the scope or meaning of the devices and methods disclosed herein.

Accordingly, the claims are not intended to be limited to the embodiments or implementations shown herein, but are to be accorded the widest scope consistent with this disclosure, the principles and the novel features disclosed herein.

What is claimed is:

1. A system, comprising:

a washable non-conductive sheet;

a plurality of electrodes, each of the plurality of electrodes being machine-washable, reusable, and conductive;

a controller configured to provide stimulation signals to each of the plurality of electrodes; and a signal pathway connecting each of the plurality of electrodes to the controller, wherein the signal pathway further comprises a controller connector;

wherein the sheet is sized and configured for a bed, wherein the plurality of electrodes are each sized and positioned to deliver the stimulation signals to a user on the bed, wherein the plurality of electrodes, comprises a first electrode comprising a substantially U-shaped outline and positioned to correspond to a location of a scapula of the user, a second electrode, larger than the first electrode, comprising a substantially W-shaped outline, and positioned to correspond to a location of a sacrum and left and right trochanters of the user, and a third electrode, smaller than the first electrode, comprising a substantially U-shaped outline, and positioned to correspond to a location of an ischial tuberosity of the user.

2. The system of claim 1, wherein at least one of the plurality of electrodes are configured to absorb moisture.

3. The system of claim 1, wherein at least one of the plurality of electrodes include an anti-microbial agent.

4. The system of claim 1, wherein the signal pathway comprises conductive wire, conductive thread, conductive ink, or combinations thereof.

5. The system of claim 1, wherein the controller is removably connected to the signal pathway with the controller connector.

6. The system of claim 1, wherein the sheet further comprises a pocket for the controller.

7. The system of claim 1, wherein:

the controller connector is a first controller connector on a first side of the sheet, and the sheet further comprises and a second controller connector on a second side of the sheet; and the controller is removably connectable to both the first controller connector and the second controller connector.

8. The system of claim 1, wherein the controller further comprises a calibration module configured to perform a calibration.

9. The system of claim 1, wherein the controller further comprises a calibration module configured to perform a calibration when the controller is removably connected to controller connector.

10. The system of claim 7, wherein the controller further comprises a calibration module configured to perform a calibration when the controller is removably connected to the signal pathway with either of the first controller connector or the second controller connector.

11. The system of claim 1, wherein the sheet is rectangular.

12. The system of claim 1, wherein the sheet has a width in the range of 99-185.5 cm (39-73 inches) and a length in the range of 193-216 cm (76-85 inches).

* * * * *